United States Patent [19]
Sanford et al.

[11] Patent Number: 5,834,264
[45] Date of Patent: Nov. 10, 1998

[54] PROCESS FOR ANAEROBIC PRODUCTION OF HYDROGEN USING A DELTA-PROTEOBACTERIUM

[75] Inventors: Robert A. Sanford, Renton, Wash.; James M. Tiedje, Lansing, Mich.; John A. Breznak, East Lansing, Mich.; John W. Urbance, Battle Creek, Mich.

[73] Assignee: Board of Trustees operating Michigan State University, East Lansing, Mich.

[21] Appl. No.: 784,083

[22] Filed: Jan. 15, 1997

Related U.S. Application Data

[62] Division of Ser. No. 629,430, Apr. 9, 1996, Pat. No. 5,705,374.

[51] Int. Cl.$^6$ ................................. C12P 3/00; C12P 1/04; B09B 3/00
[52] U.S. Cl. ...................... 435/108; 435/170; 435/262.5; 435/821
[58] Field of Search ................................. 435/168, 170, 435/821, 822, 262.5

[56] References Cited

PUBLICATIONS

Dong et al. Appl. Environ. Microbiol. vol. 60 (8), pp. 2834–2838, 1994.
Sorokin, Y. Nature. vol. 210, pp. 551–552, Abstract, 1996.
J–P. Guyot and A. Brauman, Applied and Environmental Microbiology 1436–1437 (1996).
Serfass, J.A., et al., International Journal of Hydrogen Energy 16:551–556 (1991).
Proceedings of the 1994 DOE/NREL Hydrogen Program Review, Livermore, Ca. (1994).
Klibanov, A.M., et al., Biotechnol. Bioeng. 24:25–36 (1982).
Taguchi, F., et al. Can. J. Microbiol. 41:536–540 (1995).
Bennett, M. A., et al., Journal of Solid–Phrase Biochemistry 1:137–142 (1976).
Labib, F., et a., Environ. Sci. Technol. 26:369–376 (1992).
Solomon, B.O., et al., Appl. Microbiol. Bio. 42:222–226 (1994).
Ozturk, S.S., et al., Biotechnol. Bioeng. 33:745–757 (1989).
Stams, A.J.M., Antonie van Leeuwenhoek 66:271–294 (1994).
Schink, B., et al., FEMS Microbiol. Rev. 15:85–94 (1994).
Bleicher, K., et al., Appl. Microbiol. Biotechnol. 40:910–915 (1994).
Devereux, et al., J. Bacter. 172:3609–3619 (1990).
Thauer, R.K., et al., Bacteriol. Rev. 41:170–180 (1977) (Selected pages).
Conrad, R., et al., FEMS Microb. Ecol. 38:353–360 (1986).
DeWeerd, et al (Applied and Environ. Microb. 57:1929–1934 (1991).
Boone, D. R., et al., Appl. Environ. Microbiol. 55:1735–1741 (1989).
Zhou, J., et al., Int. J. Syst. Bacteriol. 45:500–506 (1995).
Maidak, B. L., et al., Nucleic Acids Research 22:3485–3487 (1994).
Sawers, G., Antonie van Leeuwenhoek 66:57–88 (1994).
Gray, C. T., et al., Science 143:186–192 (1965).
McMahon and Chapelle, Nature 349:233–235 (1991).
Smith, et al. Arch. Microbiol. 141:8–13 (1985).
Allison et al. Arch Microbiol. 141:1–7 (1985).
Applied and Environ. Microbiol. 58:1451–1458, 1992.

*Primary Examiner*—Leon B. Lankford, Jr.
*Assistant Examiner*—Christopher R. Tate
*Attorney, Agent, or Firm*—Ian C. McLeod

[57] ABSTRACT

A process for producing hydrogen anaerobically in a culture medium or in the environment using a proteobacteria is described. Preferably the proteobacteria is *Desulfovibrio sp.* ATCC 55738 (FOX1). The hydrogen can be used as a fuel and for other purposes and is a staple chemical.

14 Claims, 18 Drawing Sheets

Phylogenetic analysis of the Delta-subdivision of the Proteobacteria, including FOX1. The tree was generated using the maximum likelihood method.

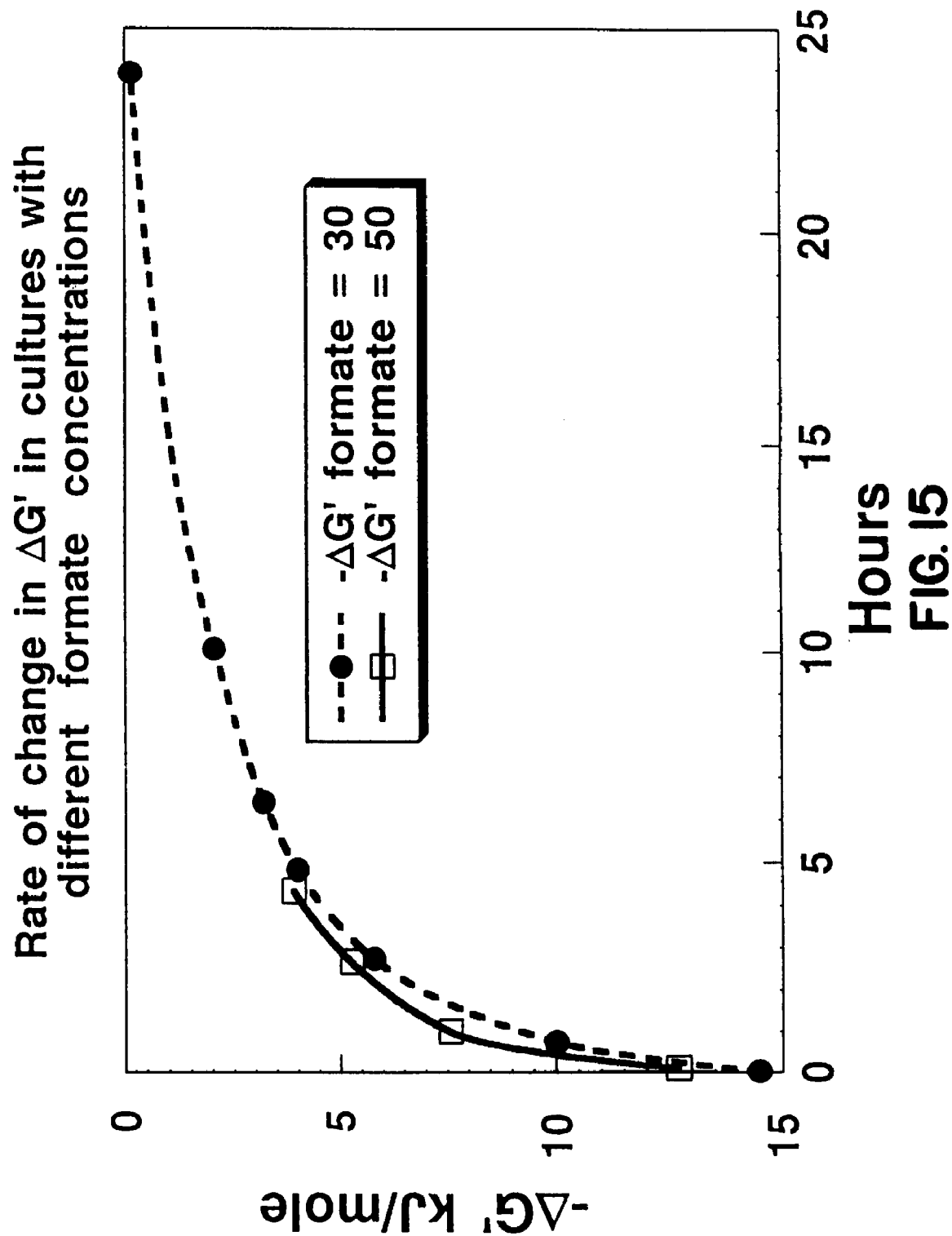

PROCESS FOR ANAEROBIC PRODUCTION OF HYDROGEN USING A DELTA-PROTEOBACTERIUM

This is a divisional of application Ser. No. 8/629,430 filed Apr. 9, 1996 now U.S. Pat. No. 5,705,374.

GOVERNMENT RIGHTS

This application was funded under National Science Foundation (NSF) Grant B1R9120006. The United States Government has certain rights under this application and any patent issuing thereon.

BACKGROUND OF THE INVENTION (1) Summary of the Invention

The present invention relates to a process for the anaerobic production of hydrogen by growth of a delta-proteobacterium on a carbon source which is selected from the group consisting of formic acid and a formate and mixtures thereof. In particular, the present invention relates to the use of a member of a family, designated as Desulfovibrionaceae, for the production of the hydrogen.

(2) Description of Related Art

Hydrogen has been described as the fuel of the future (Serfass, J. A., et al., International Journal of Hydrogen Energy 16:551–556 (1991)). It is an important feedstock in industrial processes as well as a potential source of clean energy, either for burning or in fuel cells. Although currently produced cheaply from petroleum and methanol, there are impurities that can prevent its use in some processes, such as fuel cells. Microbially generated hydrogen can provide an environmentally sound production method that is an attractive alternative to existing energy intensive technologies (Proceedings of the 1994 DOE/NREL Hydrogen Program Review, Livermore, Calif. (National Renewable Energy Laboratory (1994)). In the past, microbially generated hydrogen was not economical in part because of slow and/or low production rates and its susceptibility to by-product inhibition of the microbes (Klibanov, A. M. , et al., Biotechnol. Bioeng. 24:25–36 (1982); DeWeerd, et al., Applied and Environ. Microb. 57:1929–1934 (1991); Taguchi, F. et al., Can. J. Microbiol. 41:536–540 (1995)). In addition, light is required in many of these biological processes, which may be impractical in some circumstances. Microbial processes for hydrogen and production are shown by (Proceedings of the 1994 DOE/NREL Hydrogen Program Review, Livermore, Calif. (National Renewable Energy Laboratory (1994); Klibanov, A. M., et al., Biotechnol. Bioeng. 24:25–36 (1982); Bennett, M. A., et al., Journal of Solid-Phase Biochemistry 1:137–142 (1976); Labib F., et al., Environ. Sci. Technol. 26:369–376 (1992); and Solomon, B. O., et al., Appl. Microbiol. Biotechnol. 42:222–226 (1994)).

Formate and hydrogen have been historically viewed as energetically equivalent in anaerobic microbial systems (Ozturk, S. S., et al., Biotechnol. Bioeng. 33:745–757 (1989); Stams, A. J. M., Antonie van Leeuwenhoek 66:271–294 (1994); and Schink, B., et al., FEMS Microbiol. Rev. 15:85–94 (1994); Bleicher, K., et al., Appl. Microbiol. Biotechnol. 40:910–915 (1994)). This has led to incorrect assumptions regarding the extent of hydrogen generation in such systems.

OBJECTS

It is therefore an object of the present invention to provide a process for the anaerobic microbial production of hydrogen. It is further an object of the present invention to provide a process which is safe, economical and commercially viable. These and other objects will become increasingly apparent by reference to the following description and the claims.

BRIEF DESCRIPTION OF DRAWINGS

FIG. 15 is a graph showing that the rate of change in the free energy is the same at the different formate concentrations of FIG. 13A and 14A. The result is that rate of formate oxidation is faster at higher formate concentrations.

DESCRIPTION OF PREFERRED EMBODIMENTS

Figure 1A:
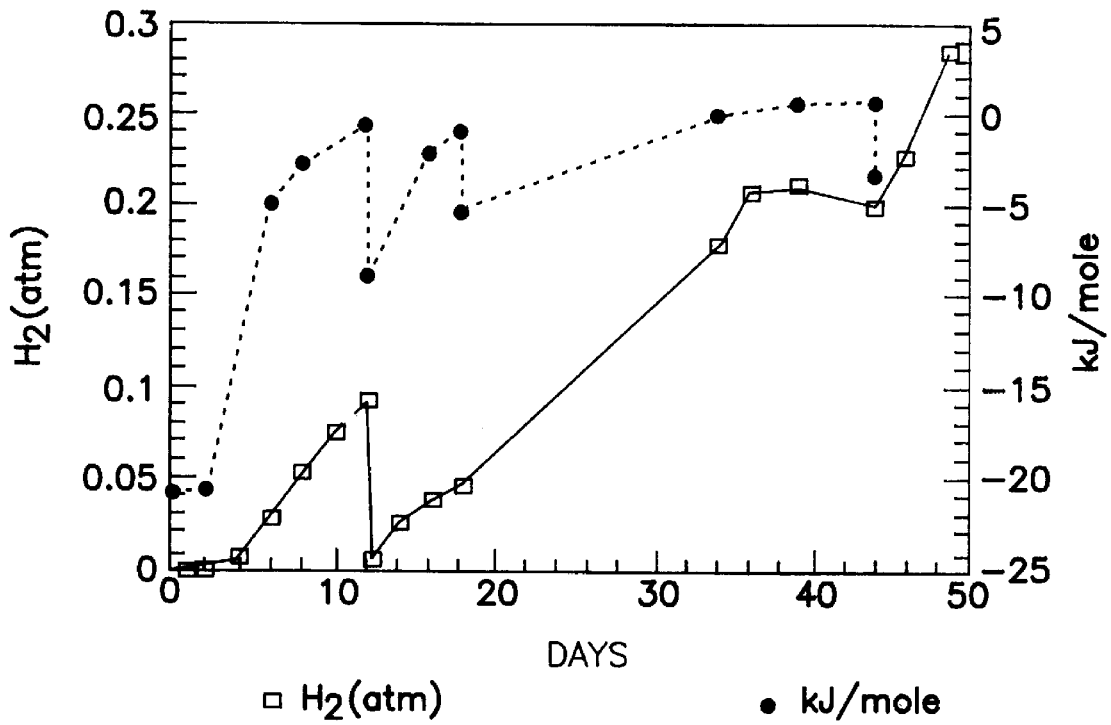
FIG. 1A is a graph showing the production of $H_2$ and corresponding $\Delta G'$ by an anaerobic formate oxidizing culture, designated herein as FOX1. Decreases in the $\Delta G'$ correspond to the removal of $H_2$ from the headspace or to the addition of formate.

The present invention relates to a process for producing hydrogen and carbon dioxide which comprises: introducing a delta-proteobacteria, having anaerobic growth characteristics with formate as a sole energy source of a representative proteobacterium deposited as ATCC 55738 (FOX1) for producing hydrogen, into a culture medium containing a first carbon source selected from the group consisting of formic acid, a formate and mixtures thereof, and in addition a nitrogen source and vitamins; and growing the delta-proteobacteria under anaerobic conditions in a confined space and in the culture medium to produce the hydrogen and carbon dioxide.

The present invention also relates to a method for remediating an environment containing a first carbon source selected from the group consisting of formic acid, formate and mixtures thereof which comprises introducing a proteobacterium selected having anaerobic growth characteristics of a representative proteobacterium deposited as ATCC 55738 (FOX1) into the environment so that hydrogen is produced in the environment which is utilized by a second bacterium in the environment.

The present invention relates to the proteobacterium deposited as ATCC 55738 (FOX1). Strain FOX1 generates $H_2$ from formic acid in the dark in a self-sustaining process in absence of another carbon source. It has an acid tolerance down to about pH 4. Hydrogen was produced by this culture at sustained rates up to an order of magnitude higher than generally reported for the prior art microbial systems discussed above.

Delta proteobacterium strain FOX1 was deposited with the American Type Culture Collection, Rockville, Md. 20852 under the Budapest Treaty on Feb. 7, 1996 as ATCC 55738. The strain is available upon request by name and number. FOX1 is a close relative of members of the Desulfovibrio genus. Based on a phylogenetic analysis FOX1 is clearly not in the same genera as other Desulfovibrio strains that have had 16S rDNA sequenced. The similarity matrix of Table 1 shows that the closest relative is *D. africanus* at 88%.

TABLE 1

Similarity Table for Proteobacter
(Includes 5' end)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1: Rh. legum | | | | | | | | | | | | | | | | | | | | | | | | |
| 2: Bur. cepaci | 81.0 | | | | | | | | | | | | | | | | | | | | | | | |
| 3: E. coli | 80.8 | 81.2 | | | | | | | | | | | | | | | | | | | | | | |
| 4: Dsv. des N4 | 81.8 | 77.9 | 79.4 | | | | | | | | | | | | | | | | | | | | | |
| 5: Dmb. bacul | 81.5 | 77.7 | 78.9 | 98.6 | | | | | | | | | | | | | | | | | | | | |
| 6: Dmb. escam | 82.2 | 78.2 | 79.7 | 97.9 | 97.8 | | | | | | | | | | | | | | | | | | | |
| 7: Dsv. salexi | 81.4 | 76.7 | 78.8 | 85.3 | 85.3 | 85.3 | | | | | | | | | | | | | | | | | | |
| 8: Dsv. des E1 | 79.9 | 76.8 | 78.9 | 86.4 | 86.2 | 87.1 | 89.0 | | | | | | | | | | | | | | | | | |
| 9: Dsv. longus | 80.8 | 77.9 | 78.7 | 86.4 | 86.2 | 86.0 | 88.4 | 87.9 | | | | | | | | | | | | | | | | |
| 10: Dsv. africa | 80.3 | 77.7 | 79.0 | 86.4 | 86.4 | 87.0 | 86.3 | 87.6 | 87.6 | | | | | | | | | | | | | | | |
| 11: Dsv. gigas | 79.9 | 76.9 | 78.3 | 85.5 | 85.2 | 85.2 | 85.9 | 85.7 | 87.6 | 86.4 | | | | | | | | | | | | | | |
| 12: sym. Sus_s | 80.3 | 75.0 | 79.4 | 83.8 | 83.5 | 83.4 | 84.7 | 82.3 | 83.1 | 82.9 | 84.7 | | | | | | | | | | | | | |
| 13: sym. Mesc | 80.0 | 74.4 | 79.0 | 83.5 | 83.3 | 83.2 | 84.7 | 82.3 | 83.1 | 82.6 | 84.7 | 99.4 | | | | | | | | | | | | |
| 14: y. clone | 79.9 | 77.3 | 78.2 | 85.2 | 84.9 | 85.8 | 86.2 | 86.2 | 87.1 | 88.1 | 87.4 | 84.5 | 84.3 | | | | | | | | | | | |
| 15: Dsv. desul | 80.4 | 76.2 | 78.9 | 87.2 | 86.6 | 86.9 | 86.4 | 86.3 | 88.4 | 87.3 | 88.1 | 87.4 | 87.1 | 87.5 | | | | | | | | | | |
| 16: Dsv. sp PIB | 80.3 | 77.7 | 78.5 | 85.9 | 85.7 | 85.9 | 89.7 | 88.1 | 90.2 | 86.8 | 86.7 | 83.4 | 83.4 | 86.9 | 86.7 | | | | | | | | | |
| 17: Dsv. sp Tes | 80.8 | 77.5 | 79.0 | 86.0 | 85.8 | 86.1 | 90.0 | 88.6 | 90.2 | 86.9 | 86.8 | 83.8 | 83.8 | 87.3 | 87.0 | 98.8 | | | | | | | | |
| 18: Dsv. vulga | 79.9 | 75.7 | 78.1 | 85.0 | 85.0 | 85.7 | 86.8 | 86.2 | 87.3 | 87.4 | 86.6 | 84.9 | 84.7 | 87.3 | 90.0 | 86.7 | 86.5 | | | | | | | |
| 19: Dsv. lomrc | 80.5 | 76.4 | 78.1 | 85.9 | 85.6 | 86.6 | 86.0 | 84.7 | 87.4 | 86.3 | 88.5 | 86.3 | 86.1 | 87.3 | 91.1 | 86.7 | 86.9 | 94.0 | | | | | | |
| 20: Dsv. sp PT2 | 80.6 | 76.5 | 77.7 | 85.4 | 85.0 | 86.3 | 86.2 | 84.7 | 87.5 | 86.7 | 88.0 | 86.1 | 85.9 | 87.2 | 90.9 | 87.0 | 87.2 | 94.4 | 98.6 | | | | | |
| 21: Dsr. acetiv | 78.4 | 76.2 | 76.0 | 78.6 | 78.2 | 78.6 | 78.6 | 78.0 | 80.0 | 79.5 | 79.5 | 76.6 | 76.4 | 79.3 | 79.0 | 78.8 | 78.5 | 78.8 | 79.7 | 80.1 | | | | |
| 22: Geo. metal | 80.7 | 80.0 | 82.8 | 83.5 | 83.2 | 84.0 | 80.6 | 81.9 | 81.5 | 82.5 | 82.1 | 81.8 | 81.4 | 83.8 | 83.0 | 80.6 | 80.9 | 81.8 | 82.4 | 82.2 | 78.3 | | | |
| 23: Dmn. tiedj | 82.0 | 79.3 | 79.3 | 81.0 | 80.5 | 81.0 | 80.0 | 80.8 | 82.4 | 80.4 | 80.3 | 79.0 | 79.0 | 82.7 | 80.5 | 82.3 | 82.1 | 78.7 | 79.3 | 79.4 | 78.4 | 85.7 | | |
| 24: Dsb. postg | 78.6 | 76.2 | 77.5 | 83.1 | 82.6 | 82.9 | 80.8 | 82.0 | 81.9 | 80.9 | 81.6 | 80.5 | 80.3 | 81.2 | 82.3 | 80.5 | 80.7 | 79.0 | 79.8 | 79.3 | 79.4 | 82.0 | 81.8 | |
| 25: Hel. pylori | 76.2 | 76.5 | 75.1 | 78.4 | 78.3 | 78.3 | 77.3 | 76.9 | 78.6 | 77.4 | 79.0 | 78.5 | 78.3 | 77.5 | 79.1 | 77.6 | 77.9 | 78.6 | 79.2 | 79.2 | 78.4 | 76.9 | 77.1 | 76.3 |

Figure 5:
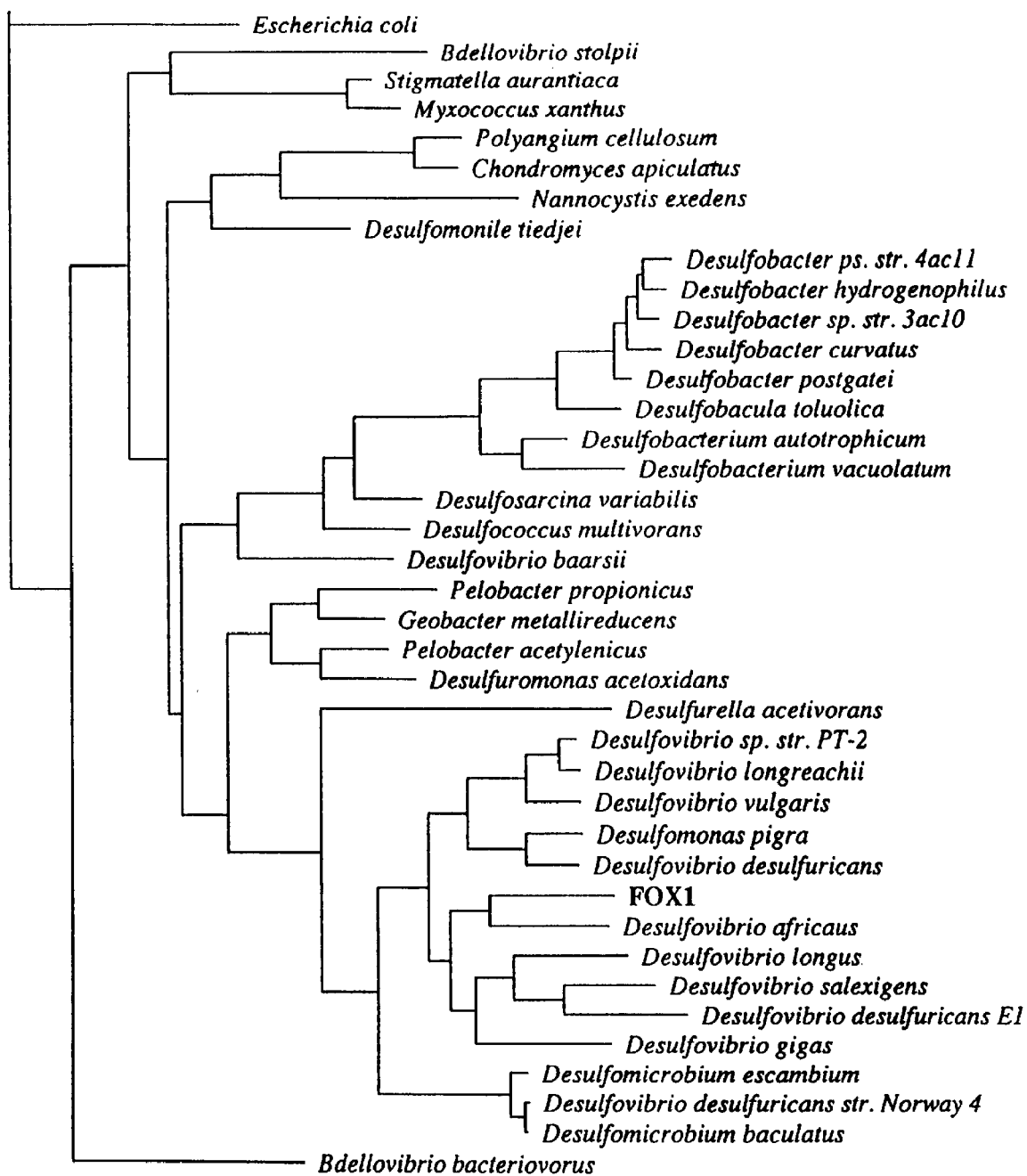
FIGS. 5 and 6 are phylogenetic trees showing nearest related delta-proteobacteria to formate-oxidizing strain FOX1.
Figure 6:
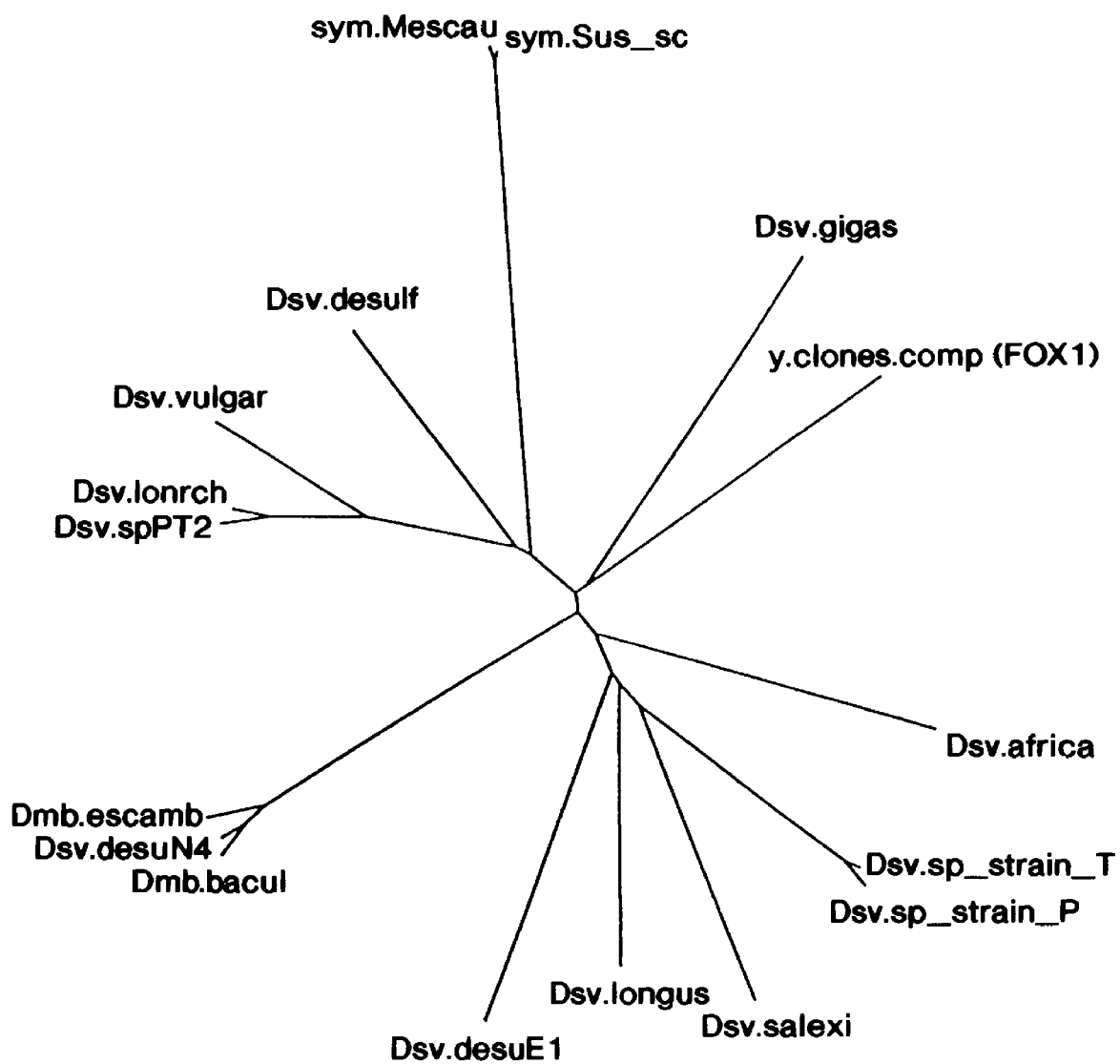

This is clearly not close enough to designate FOX1 as a member of the same genus. Research on the phylogeny of this group has proposed that FOX-1 belongs to a phylogenetically coherent family consisting of several genera as shown in FIGS. 5 and 6. This family name proposed is Desulfovibrionaceae (Devereux, et al. J. Bacter. 172:3609–3619 (1990)).

The growth characteristics exhibited by FOX1 are typical for sulfate reducers in the family of Desulfovibrionaceae. Despite phylogenetic diversity few physiological differences of taxonomic value exist. FOX1 is reliably characterized based on its phylogeny and its ability to generate hydrogen. The growth substrates for FOX1 are:

1. Formate (10–40 mM0 plus acetate (1 mM) for the generation of hydrogen; 2. Pyruvate fermentation: pyruvate (12 mM) supports growth and is fermented to approximately 9 mM acetate, 3 mM succinate and a trace amount of hydrogen; 3. Lactate plus sulfate or thiosulfate (5 mM each): Lactate oxidation to acetate is coupled to the reduction of sulfate or thiosulfate to sulfide. Some evidence exists that sulfite may also be used as an electron acceptor; and 4. Formate (30 mM) plus sulfate or thiosulfate (5 mM): Growth is same as with lactate if acetate (1 mM) is included in the medium.

The preferred growth conditions for strain FOX1 are in a culture medium containing:

Salts: 2 mM potassium phosphate (buffer pH 7.2). $CaCl_2 \cdot 2H_2O$ 0.015 g/l; $MgCl_2 \cdot 6H_2O$ 0.02 g/l; $FeSO_4 \cdot 7H_2O$ 0.007 g/l; $Na_2SO_4$ 0.005 g/l.

Trace metals (mg/l): $Mn/Cl_2 \cdot 4H_2O$ (5 mg); $H_3BO_3$ (0.5 mg); $ZnCl_2$ (0.5 mg); $CoCl_2 \cdot 6H_2O$ (0.5 mg); $NiSO_4 \cdot 6H_2O$ (0.5 mg); $CuCl_2 \cdot 2H_2O$ (0.3 mg); and $NaMoO_4 \cdot 2H_2O$ (0.1 mg).

Tungsten and selenium (mg/l): $Na_2SeO_4$ (0.003 mg); and $Na_2WO_4$ (0.008 mg); 6 mM $NH_4Cl$ (nitrogen source).

Vitamin solution (mg/l): biotin (0.02 mg); folic acid (0.02 mg); pyridoxine HCl (0.1 mg); riboflavin (0.05 mg); thiamine (0.05 mg); nicotinic acid (0.05 mg); panthenic acid (0.05 mg); vitamin $B_{12}$ (0.01 mg); p-aminobenzoic acid (0.05 mg); and thioctic acid (0.05 mg).

Reductants: Na-cysteine or Na-sulfide together or alone (0.2–0.4 mM combined concentration).

Anaerobic food webs often terminate in methanogenic or acetogenic processes. The generation of methane or acetate requires the presence of a suitable electron source, usually $H_2$ or formate. Historically these two electron donors have been viewed as equivalents in an anaerobic environment since thermodynamically they are essentially in equilibrium under standard conditions. Unfortunately the prior art has been too complacent in the past and have easily assigned energetic relationships among microorganisms based on free energy calculations ($\Delta G^{o'}$) made using standard conditions. In the real world the equilibrium between formate and hydrogen as well as many other compounds are controlled by environmental conditions. A series of experiments and calculations with FOX1 show that formate to hydrogen conversion is exergonic ($-\Delta G'$) under reasonable environmental conditions (i.e. like those expected within an anaerobic environment). This has led to an alternative flow of energy in anaerobic food webs in which formate is converted to hydrogen, a process releasing sufficient energy to support growth of FOX1.

EXAMPLE 1

FOX1 was obtained from an anaerobic microcosm which showed reductive dechlorination activity for ortho-chlorophenol and meta-chlorophenol. An analysis of the headspace of this enrichment had shown significant concentrations of $H_2$ (0.03 atm) and only trace amounts of methane. Both the dechlorination activity and $H_2$ producing activity were serially transferred twice in enrichment cultures before an effort was made to isolate colonies on anaerobic medium. This medium contained a mixture of volatile fatty acids (VFAs) consisting of formate, succinate, propionate, butyrate and fumarate (as an electron acceptor). The colonies that grew on these plates were subsequently transferred as a mixed culture back into anaerobic broth containing the VFAs and chlorophenols. Although no dechlorination activity occurred over several months, significant hydrogen production was measured along with the depletion of formate and succinate. Subsequent transfers of this culture have shown that formate alone supported the production of hydrogen, although this activity was stimulated when acetate is added to the medium. FOX1 culture was transferred greater than ten times using a 0.1–1.0% inoculum without change. Autoclaved controls containing cells exhibited no $H_2$ evolution.

To show that the $H_2$ production from formate was supplying energy to a growing microbial population of the FOX1, the concentrations of formate, $H_2$ and $CO_2$ were monitored during incubation. The $\Delta G'$ was calculated at each data point using the formula below which adjusts free energy to environmental conditions from standard conditions $\Delta G^{o'}$ (Thauer, R. K., et al., Bacteriol. Rev. 41:100–180 (1977)).

$HCOO^- \rightarrow HCO_3^- + H_2$  $\Delta G^{o'} = +1.3$ kJ/mole

For example: 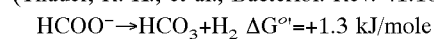
$\Delta G' = \Delta G^{o'} + 2.52 \ Ln([HCO_3^-]\cdot[H_2])-2.52 \ Ln([HCOO^-])$ When formate=0.01M, $HCO_3^-$=0.01M (reasonable for an anoxic environment (Conrad, R., et al., FEMS Microb. Ecol. 38:353–360 (1986)), and $H_2$=0.0001 atm (reasonable for methanogenic conditions). Temp.=30° C.

$\Delta G' = -21.9$ kJ/mole

Figure 1B:
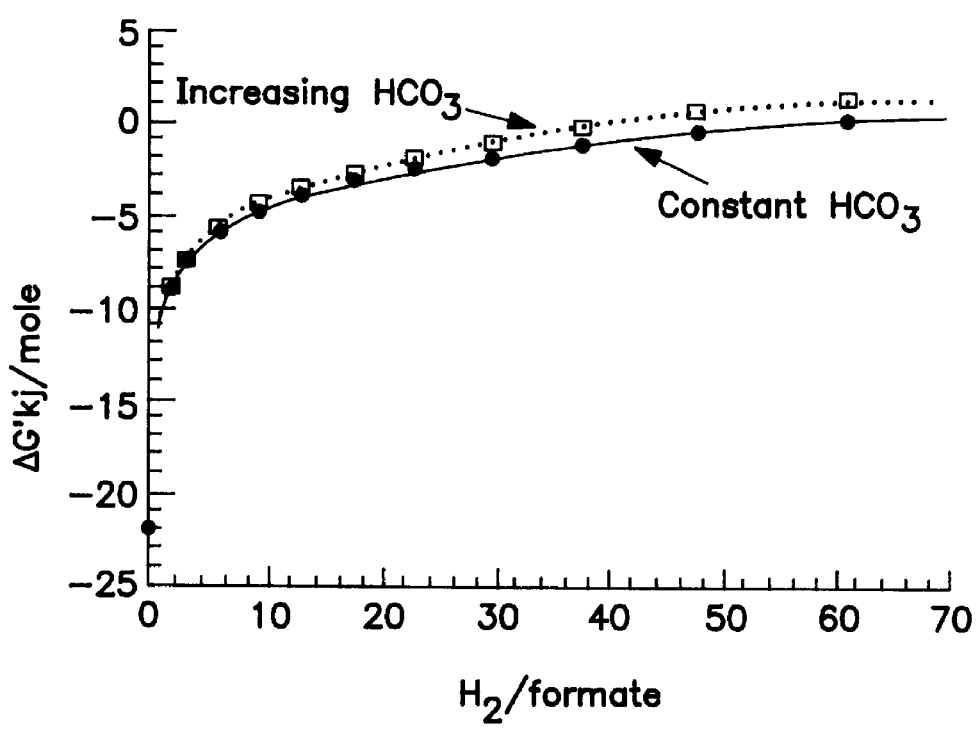
FIG. 1B is a graph showing the theoretical free energy $\Delta G'$ available from the oxidation of formate by FOX1 as a function of the mole ratio of $H_2$ (atm) to formate. Initial bicarbonate concentration was 10 mM, formate was 10 mM and $H_2$ was 0.0001 atm. $H_2$ and formate reached equilibrium at a mole ratio of 40:1 under increasing $HCO_3^-$. The ratio of $H_2$ atm to formate changes during the formate oxidation.

FIG. 1A shows the $H_2$ concentrations and the $\Delta G'$ in a culture over a long incubation period. The $\Delta G'$ was manipulated by purging out the headspace with Argon or adding additional formate. In both cases the rate of $H_2$ production increased in response to the lower $\Delta G'$. It is also evident from FIG. 1A that the concentrations of $H_2$ and formate reached thermodynamic equilibrium. This is another unique feature of FOX1. Experiments have shown that equilibrium is reached independent of the initial formate concentration and that $H_2$ concentrations as high as 120 kPa have been observed. The rate of hydrogen generation was also significantly increased under shaking conditions. FIG. 1B shows the relationship between the $\Delta G'$ and the molar ratio of $H_2$ in atm to formate when the above initial conditions were considered. This shows that a ratio of about 40:1 was required to reach thermodynamic equilibrium.

This Example demonstrates the feasibility of formate serving as an energy source for anaerobic growth, with stoichiometric production of hydrogen. The fact that the activity was serially transferred greater than ten (10) times and a characteristic lag was exhibited before activity was observed indicated that growth is likely to be occurring. The counts provide direct evidence for growth.

EXAMPLE 2

Hydrogen is also important in anaerobic food webs that usually terminate in methanogenic or acetogenic processes. The generation of methane or acetate requires the presence of a suitable electron source usually $H_2$ or formate. Obligate syntrophic microorganisms rely on methanogens to consume the $H_2$ they produce. This interspecies $H_2$ transfer is a fundamental component of anaerobic food webs terminating in methanogenesis (Stams, A. J. M., Antonie van Leeuwenhoek 66:271–294 (1994); and Conrad, R., et al., FEMS Microbiol. Ecol. 38:353–360 (1986)). Many researchers have proposed that formate transfer would be energetically equivalent and more likely than $H_2$ transfer mainly due to its greater solubility (Ozturk, S. S., et al., Biotechnol. Bioeng. 33:745–757 (1989); Stams, A. J. M., Antonie van Leeuwenhoek 66:271–294 (1994); and Boone, D. R., et al., Appl. Environ. Microbiol. 55:1735–1741 (1989)). Microbiologists and engineers treated these two electron donors as energetically equivalent because they are close to thermodynamic equilibrium under standard conditions (Thauer, R. K., et al., Bacterial. Rev. 41:100–180 (1977); and Ozturk, S. S., et al., Biotechnol. Bioeng. 33:745–757 (1989))?????.

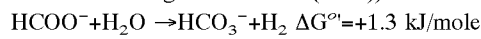

However formate, $H_2$ and $CO_2$ are not likely to be in equilibrium in the environment. When reasonable environmental conditions are considered this slightly endergonic reaction becomes exergonic. The formate oxidizing culture FOX1 confirms this theoretical consideration, since it grows using formate as its sole energy source. To calculate the $\Delta G'$ the following formula was used:

$\Delta G' = \Delta G^{o\prime} + 2.52*Ln([HCO_3^-]*[H_2]) - 2.52*Ln[HCOO^-]$

Figure 2:
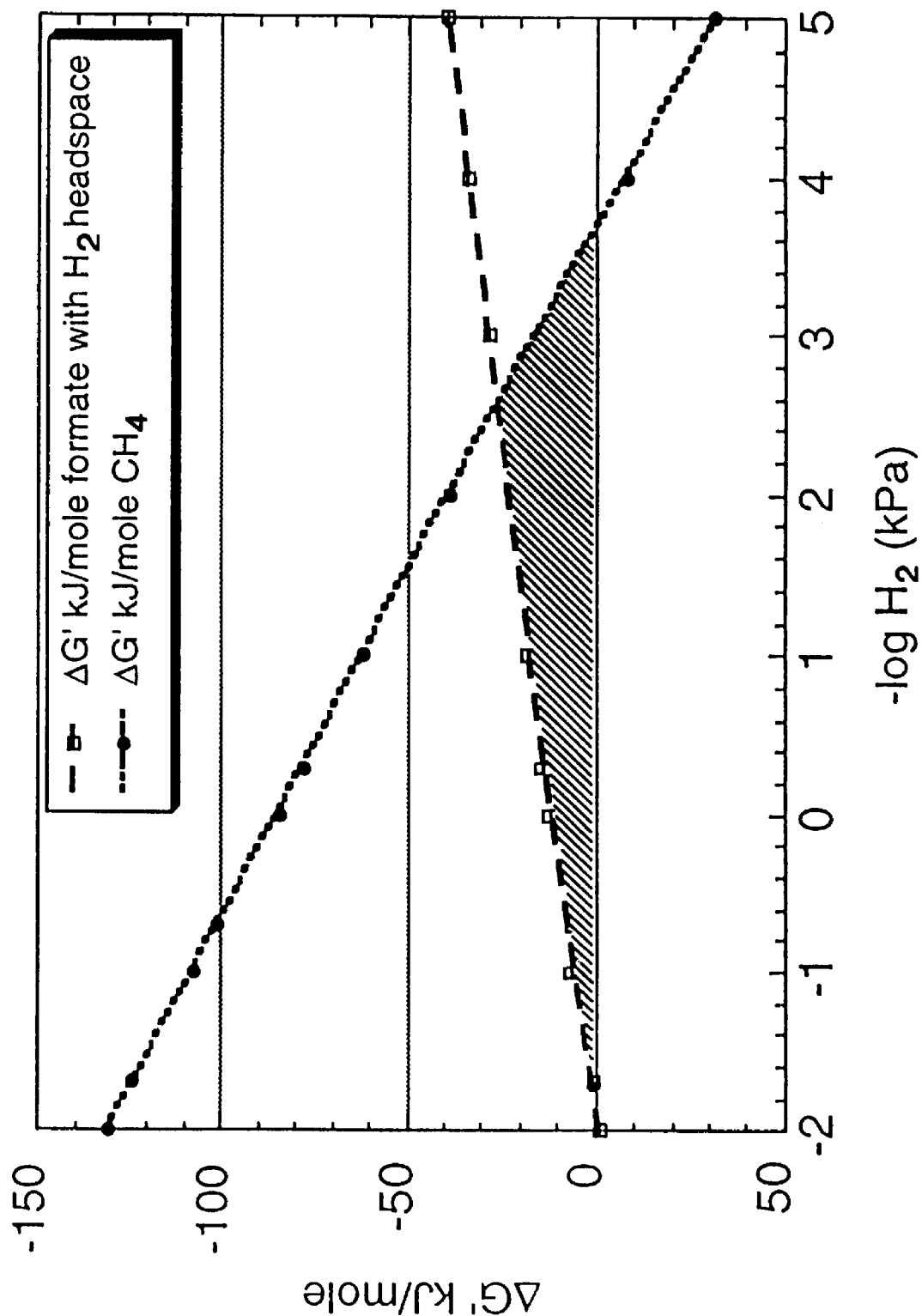
FIG. 2 is a graph showing the energy relationship between hydrogen and methane production with FOX1 at various pressures. It shows that formate oxidation is energetically favorable at concentrations of hydrogen up to 100 kPa under the starting conditions of FIG. 1.

FIG. 2 shows that at pH 7.0 with formate and $HCO_3^-$ at 0.01M this reaction is exergonic for all $H_2$ concentrations under 100 kPa (1 atm). The $\Delta G'$ is −21.9 kJ when the initial $H_2$ partial pressure is 0.01 kPa. Under these initial conditions it is clearly not energetically favorable to convert $H_2$ and $CO_2$ into formate. Hence, interspecies $H_2$ transfer should be favored over formate transfer, when excess formate is present. This implies that there may be a thermodynamic constraint on interspecies formate transfer with $H_2$ clearly being preferred. Since there is energy available from formate oxidation, it is reasonable to find that a somewhat specialized microorganism has evolved the capability to couple growth to this process.

EXAMPLE 3

Figure 3A:
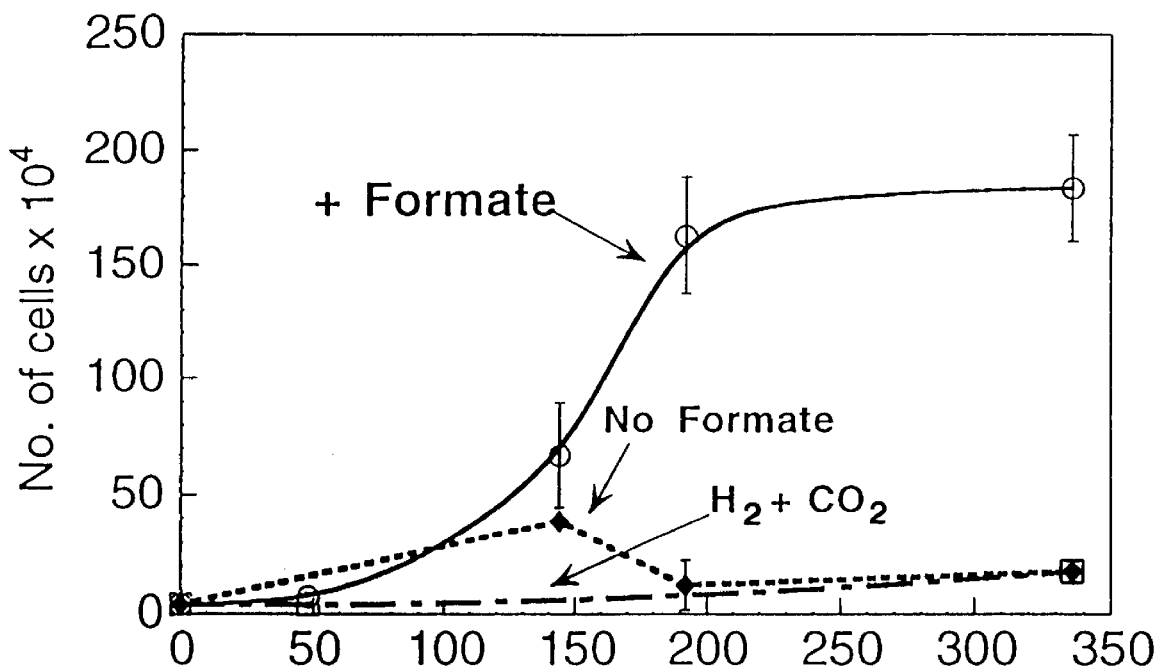
FIG. 3A is a graph showing growth of anaerobic formate oxidizing bacterium FOX-1 as measured by direct microscopic counts of acridine orange stained microbial cells. Controls with no formate or with $H_2$ and $CO_2$ indicate that growth only occurs when formate is present.
Figure 3B:
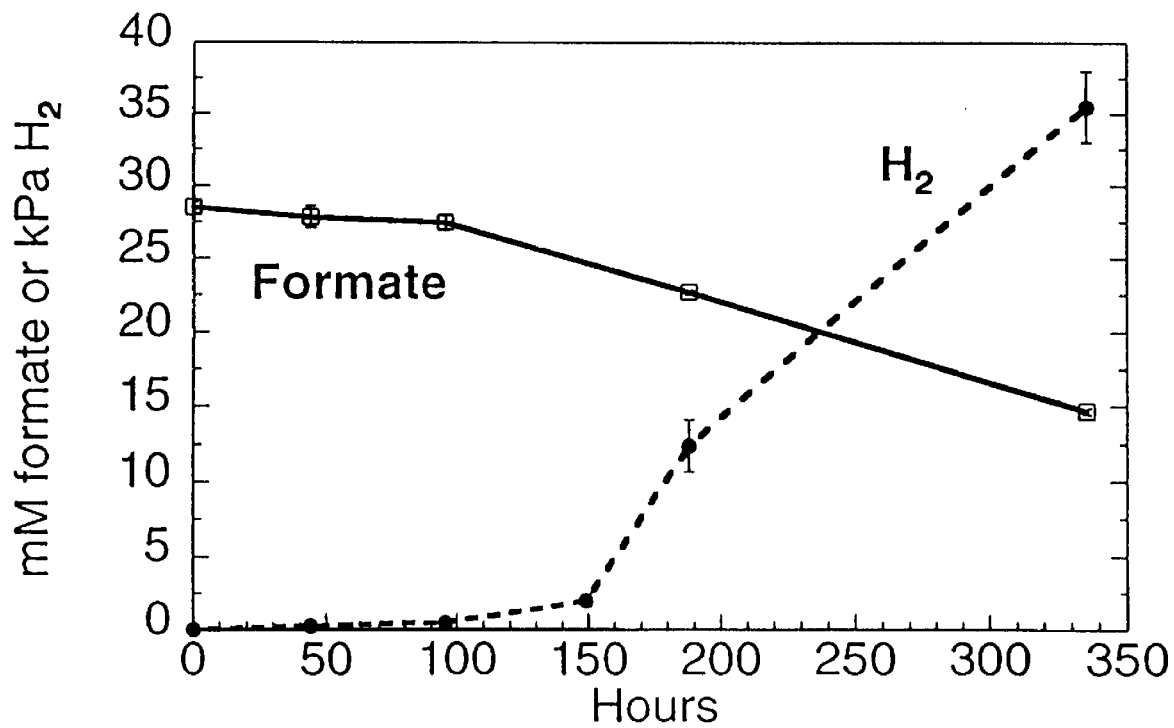
FIG. 3B is a graph showing the loss of formate from cultures and the subsequent stoichiometric production of $H_2$. Culture volume was 100 ml with a headspace of 60 ml. Error bars indicate the 95% confidence intervals for triplicate cultures.
Figure 4:
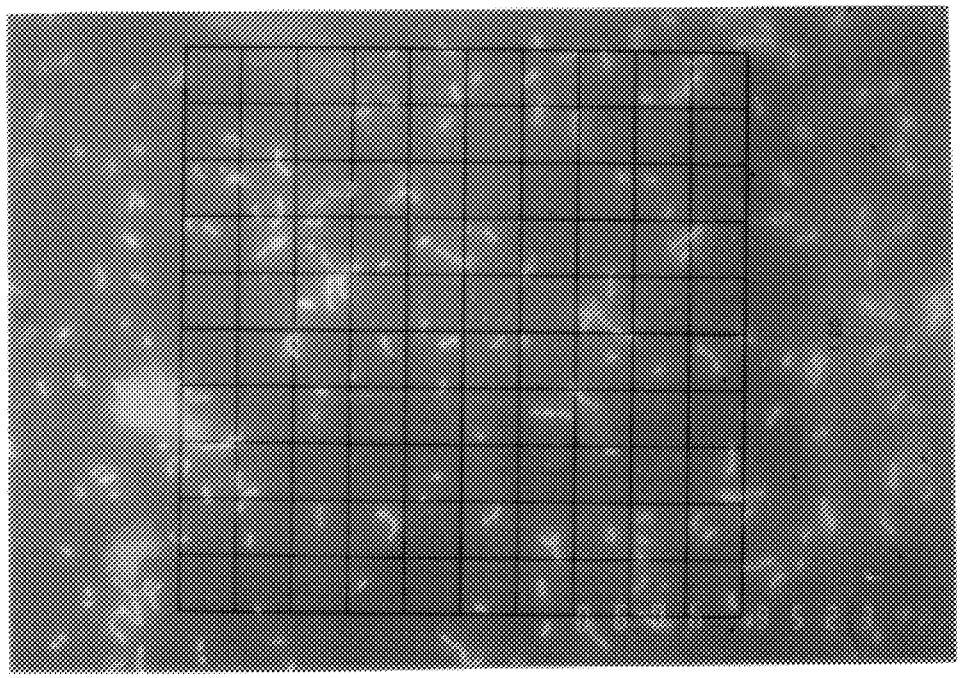
FIG. 4 is a microscopic image of formate-oxidizing anaerobic bacterium FOX1. Reference boxes are $13^2 \mu^2$. The average size of the cells in the culture is $2\mu$ wide and 3 to $5\mu$ long.

To prove that anaerobic formate oxidation supported actual growth of FOX1, direct microscopic counts of acridine orange stained cells were made by taking samples at different time intervals (FIG. 3A). Controls without formate or with $H_2$ and $CO_2$ did not show appreciable increases in cell numbers. The doubling time was 30 hours. Autoclaved controls containing cells with formate and acetate exhibited no $H_2$ evolution. FIG. 3B shows that as formate was consumed stoichiometric quantities of $H_2$ were evolved from the same culture. No acetate or other VFAs were produced by this culture. The $H_2$ evolution rate in batch cultures was 7300 ml per h-g protein and the cell yield was 20.9 $\mu$g protein per mmol formate consumed. Microscopic observations of cells in stationary phase showed that FOX1 is pleomorphic after growth as shown by FIG. 4. In contrast, growth of this strain on pyruvate results in little variation in cell morphology. This may be due to the limited energy available from formate oxidation. It is possible that formate may promote a type of stress-related growth which resulted in abnormal cell-types.

EXAMPLE 4

Identification and characterization of FOX1 was achieved by phylogenetic analysis using the 16S ribosomal RNA gene. A replicate of the formate-oxidizing culture was harvested by centrifugation. Cells were lysed by repeated freeze-thaw cycles and the nucleic acids purified by phenol/chloroform extraction and alcohol precipitation. Near complete (ca. 1500 bp) 16S rRNA genes were then PCR amplified using previously described primers (Zhou, J., et al., Int. J. Syst. Bacteriol. 45:500–506 (1995)). A fraction of the amplified product was cloned using a commercial kit (TA Cloning Kit, Invitrogen, San Diego, Calif.) and four of the resulting clones were then randomly selected and sequenced, along with the uncloned, amplified product. All five templates had essentially identical sequences. The identical sequences and the unambiguous sequence results from the uncloned PCR product verified that the culture consisted of a single organism. Phylogenetic analysis placed the formate-oxidizing organism within the family Desulfovibrio, in the delta-subdivision of the Proteobacteria, as illustrated in FIGS. 5 and 6 (Maidak, B. L., et al., Nucleic Acids Research 22:3485–3487 (1994)). Its nearest relative was *Desulfovibrio africanus* (88.0% similarity) as shown in Table 1. Preliminary experiments have shown that FOX1 is a sulfate reducer and therefore its physiology is consistent with its phylogeny. It is perhaps not surprising to find this organism related to the delta-subgroup of the Proteobacteria, since this group is particularly noted for its diversity of anaerobic processes.

EXAMPLE 5

Figure 7A:
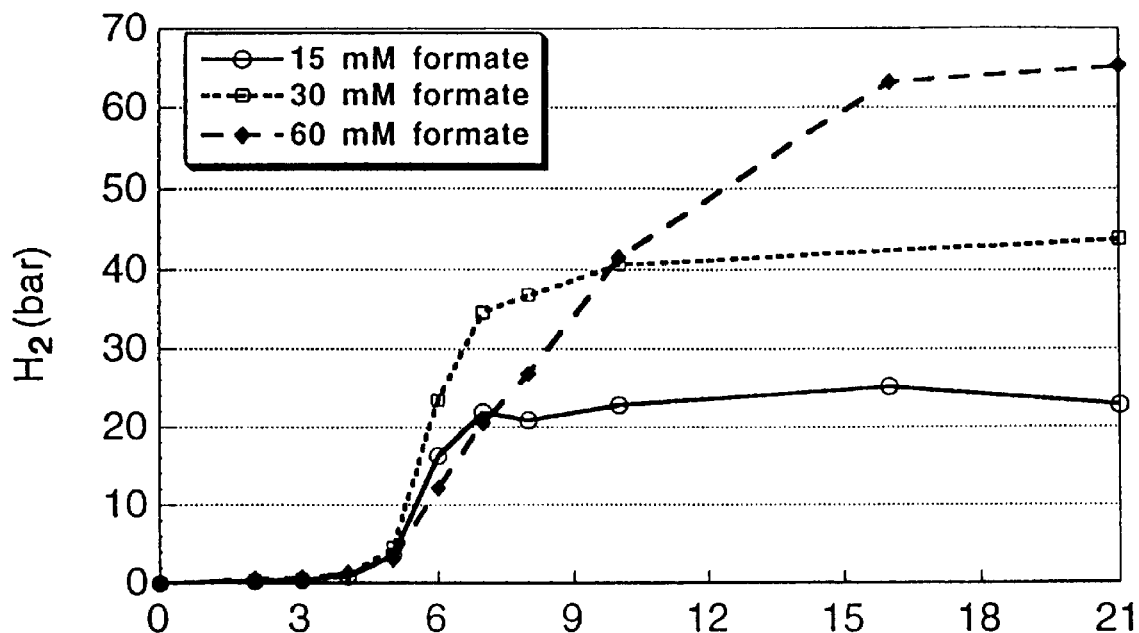
FIG. 7A is a graph showing hydrogen generated in FOX1 cultures started at three formate concentrations: 15 mM, 30 mM and 60 mM. Graphically represented is the average partial pressure for $H_2$ in duplicate cultures. Hydrogen concentration reached a steady state in all cultures after 20 days.
Figure 7B:
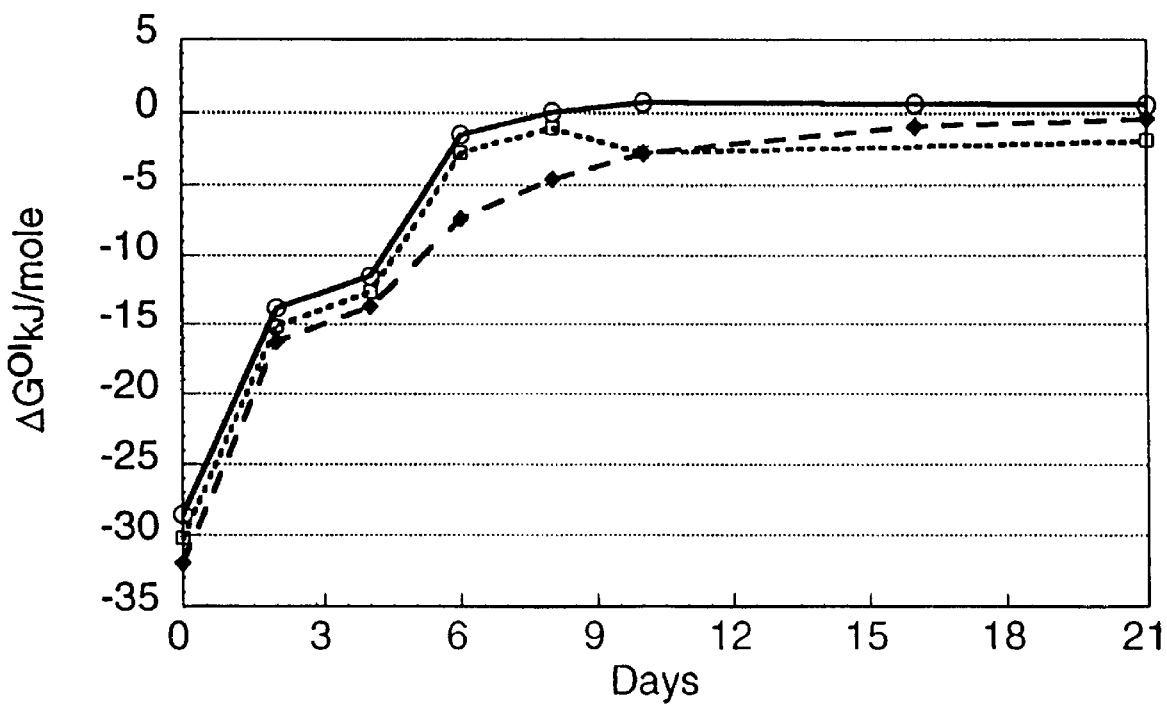
FIG. 7B is a graph showing free energy $\Delta G'$ shown for the same cultures with different initial formate concentrations. The $\Delta G'$ was calculated by measuring the $H_2$ partial pressure and determining by difference the formate and bicarbonate concentrations. Formate was measured initially and at the final data point to verify the free-energy calculations. All three cultures converge at thermodynamic equilibrium at 20 days.

Since the energy apparently available from anaerobic formate oxidation to hydrogen is minimal, it was determined whether thermodynamic equilibrium was reached. A threshold can be expected in some systems since energy may be required to initiate the process, such as transport of formate. If this were the case the free-energy for the system after $H_2$ evolution ceases would always be exergonic for formate oxidation. To determine this, cultures of the $H_2$ producer FOX1 were started with different initial formate concentrations: 15 mM, 30 mM and 60 mM. Results showed that as the initial formation concentration increased the final $H_2$ concentration increased to a high as 66 kPa with the 60 mM formate culture (FIG. 7A). In fact $H_2$ concentrations of greater than 100 kPa were obtained with similar cultures that had been refed formic acid. Regardless of the initial formate concentration the calculated $\Delta G'$ at the end of incubation was approximately 0 kJ/mole indicating that thermodynamic equilibrium had been obtained (FIG. 7B). Most of the available free-energy was used during initial formate oxidation when no $H_2$ was present. For example, when $\Delta G$ is calculated after the reaction has partially proceeded, with formate equal to 0.009M, $HCO_3^-$ at 0.011M and $H_2$ equal to 3.7 kPa, the $\Delta G'$ increases from −21.9 kJ to −6.5 kJ (assuming a 100 ml culture with a 60 ml headspace). At equilibrium under the same conditions, the $H_2$ partial pressure reaches approximately 18.5 kPa, illustrating that most of the $H_2$ evolution exhibited by this organism does not yield much energy. The ability to easily determine the free-energy under initial conditions and at equilibrium within this culture is perhaps unique for a biological process that yields energy for growth and hence may be a good model for studying the coupling of free-energy to growth.

These observations demonstrated the feasibility of formate serving as an energy source for anaerobic growth, with stoichiometric production of hydrogen. Although many microorganisms, including *E. coli*, can convert formate into $H_2$, this reaction has not been described as energetically beneficial and independent of other energy yield substrates (Sawers, G., Antonie van Leeuwenhoek 66:57–88 (1994); and Gray, C. T., et al., Science 143:186–192 (1965)). The discovery of FOX1 suggests that some of the previously described $H_2$-evolving, formate-oxidizers should be reevaluated for the potential energetic benefit of this process. Since this culture produces $H_2$ at sustained rates up to ten times those of other biological systems, this is a more attractive method for industrial $H_2$ production.

EXAMPLE 6

To further demonstrate the present invention, all cultures of FOX1 were maintained in closed 160 ml serum bottles containing 100 ml of an anaerobic basal salts medium with the following amendments: vitamin solution Na-cysteine (0.1 mM), Na-HCO$_3$ (10 mM), Na-acetate (1 mM), Na-sulfide (0.1 mM), and Na-formate (10–60 mM). Cultures were incubated on a rotary shaker in the dark at 30° C. Batch cultures were amended with formic acid on an as needed basis. The headspace was purged with argon and 3–5 ml of $CO_2$ was added separately to each culture. Hydrogen was monitored by a GC equipped with a TCD detector and formate was quantified using HPLC analysis.

Figure 8A:
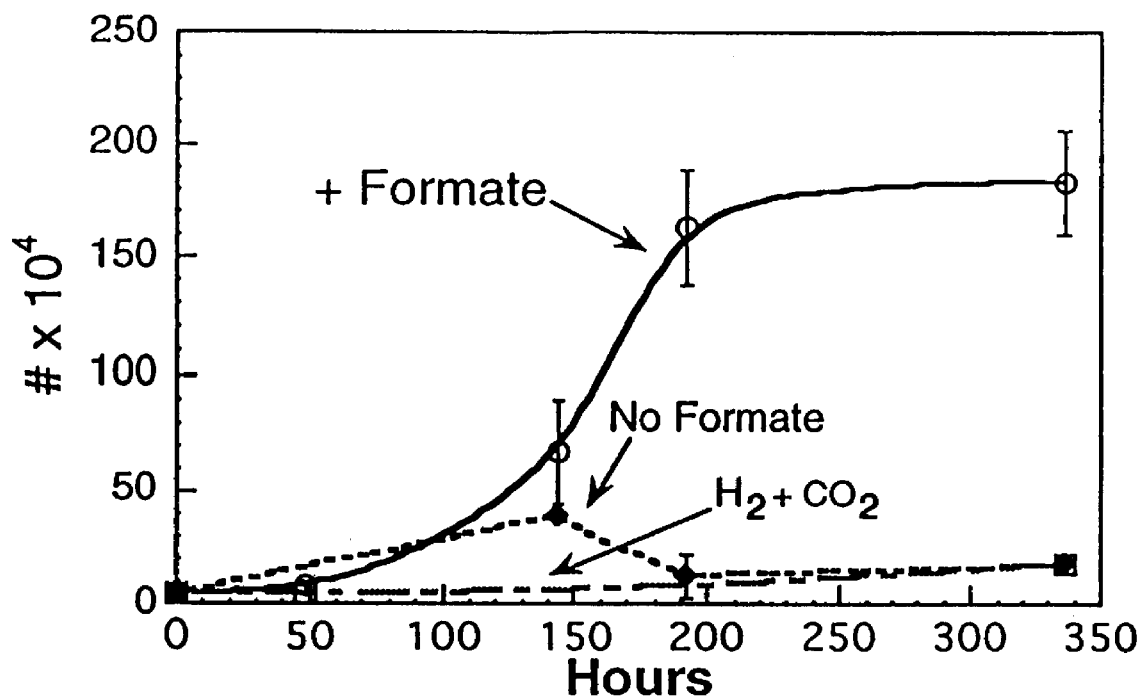
FIG. 8A is a graph showing the growth of the FOX1 culture as determined by direct microscopic counts using acridine orange as a fluorescent dye. The "No formate" control refers to triplicate cultures that received acetate only. The $H_2+CO_2$ control contained no added carbon and had a 80:20 ratio mix of these two gases. Data points are the average of triplicate cultures with the error bars representing the 95% confidence intervals.
Figure 8B:
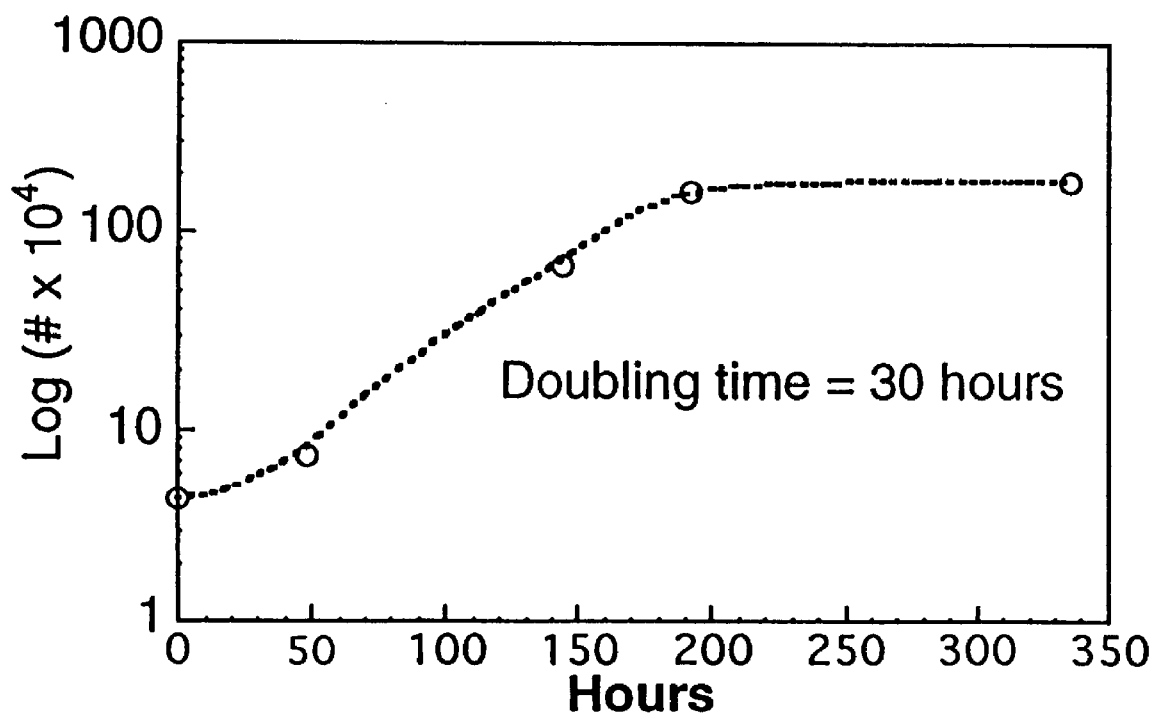
FIG. 8B is a graph showing the exponential growth phase of the formate containing culture. Initial formate, as HCOONa, was 30 mM.

Growth was shown by monitoring direct counts of acridine orange stained cells. FIGS. 8A and 8B show that growth only occurred when formate (30 mM) was present in the medium and that the doubling time in triplicate cultures was 30 hours. The cell density obtained was very low, with only $2 \times 10^6$ cells per ml being present. FIG. 7A shows the $H_2$ generation in this culture and the calculated $\Delta G'$ for each time point. This shows that formate and $H_2$ reach thermodynamic equilibrium.

Thermodynamic equilibrium ($\Delta G'$–0) was obtained in cultures regardless of the starting formate concentration (FIG. 7A and 7B). FIG. 7A shows that the $H_2$ concentration reaches 65% v/v in cultures started with 60 mM formate, but appears to have a slower gas production rate.

Figure 9:
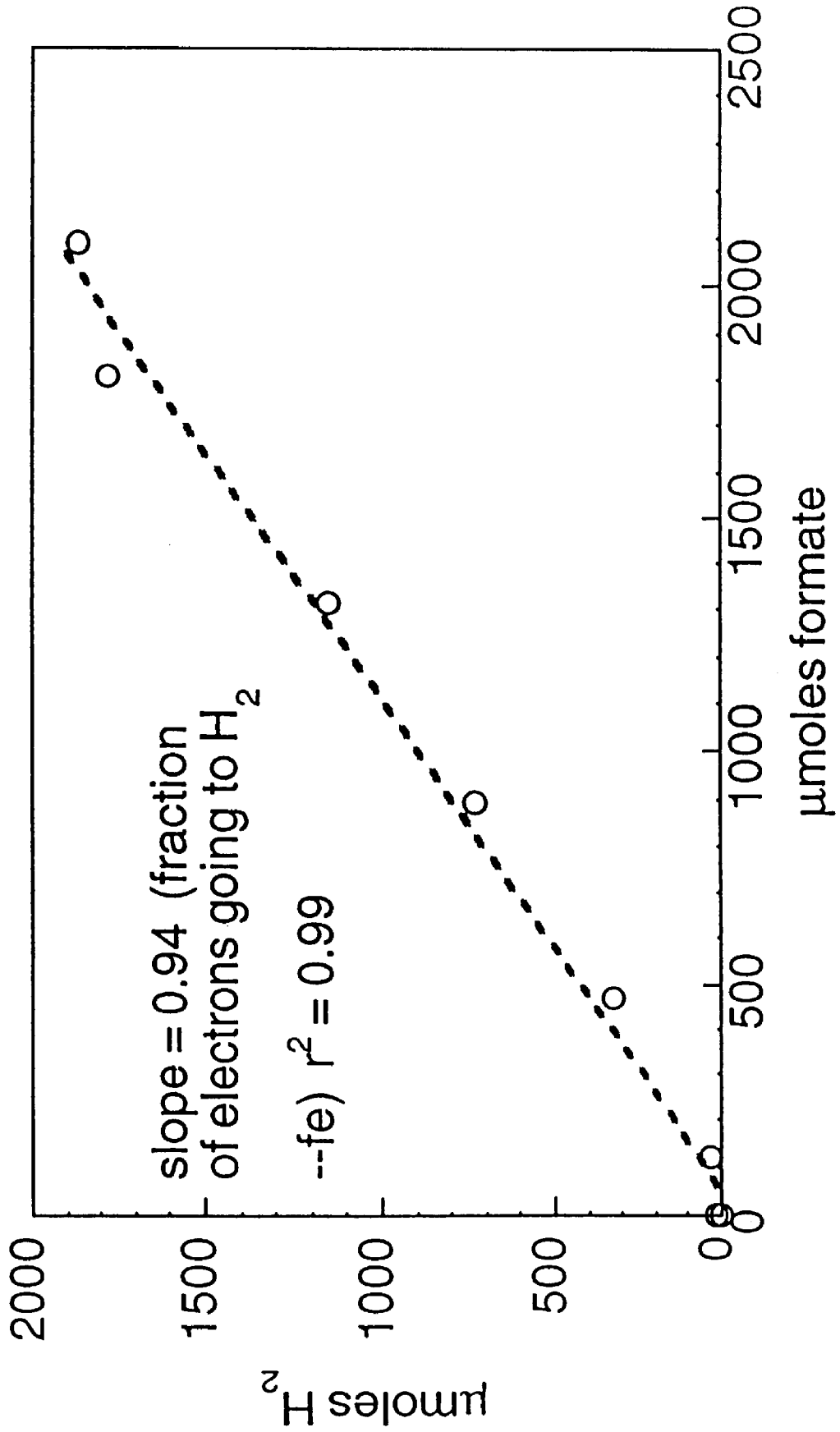
FIG. 9 is a graph showing that the fraction of electrons (fe) from formate oxidation used for $H^+$ reduction for duplicate FOX1 cultures started with 60 mM formate. The value is reasonable for a culture obtaining energy from the oxidation of formate to produce $H_2$ and $CO_2$. It shows that little energy is available for biomass and therefore biomass will be produced during formate oxidation for hydrogen production.

Formate oxidation to hydrogen is efficient, with 94% conversion (FIG. 9). This implies that formate (or formic acid) would be a good storage matrix for production of hydrogen by this anaerobic culture.

Figure 10A:
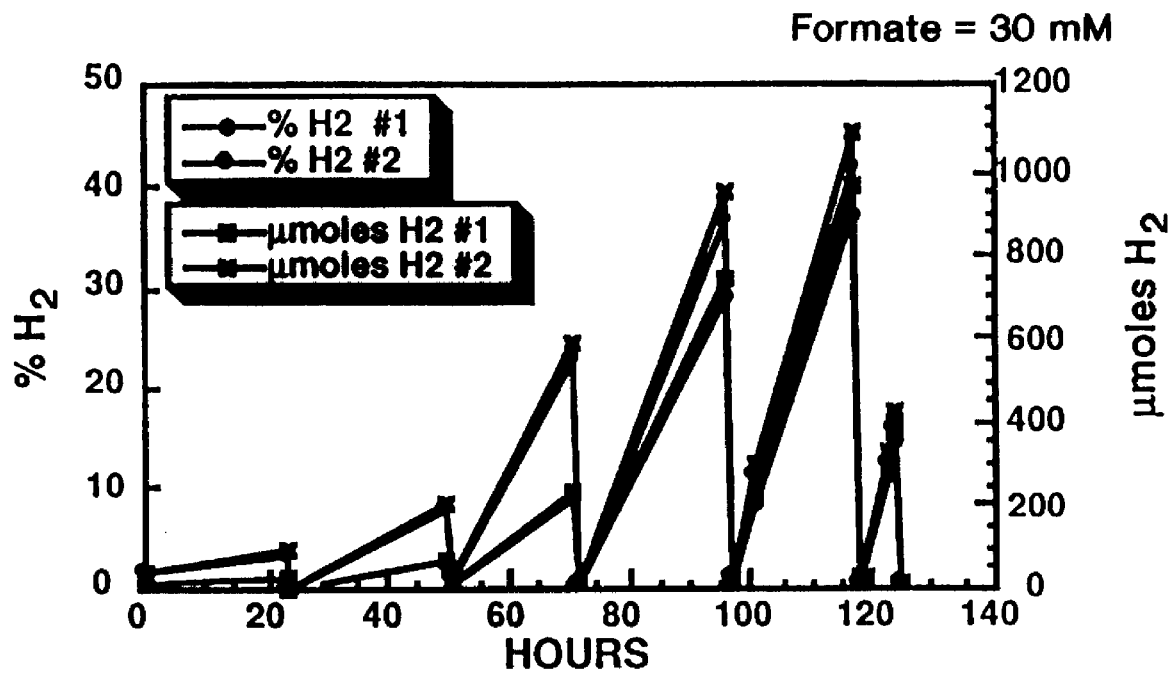
FIG. 10A is a graph showing hydrogen production in duplicate cultures of anaerobic formate oxidizer FOX1. High points indicate times when headspace was purged and additional formate was added.
Figure 10B:
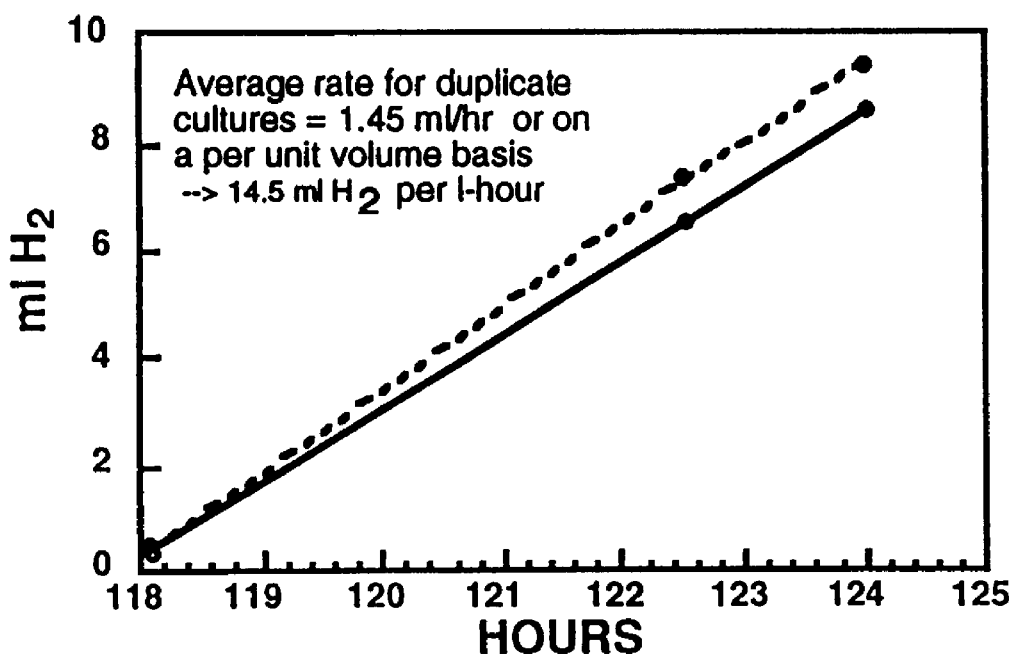
FIG. 10B is a graph showing rates of $H_2$ determined for a culture of FOX1 containing approximately $10^7$ cells per ml.
Figure 11:
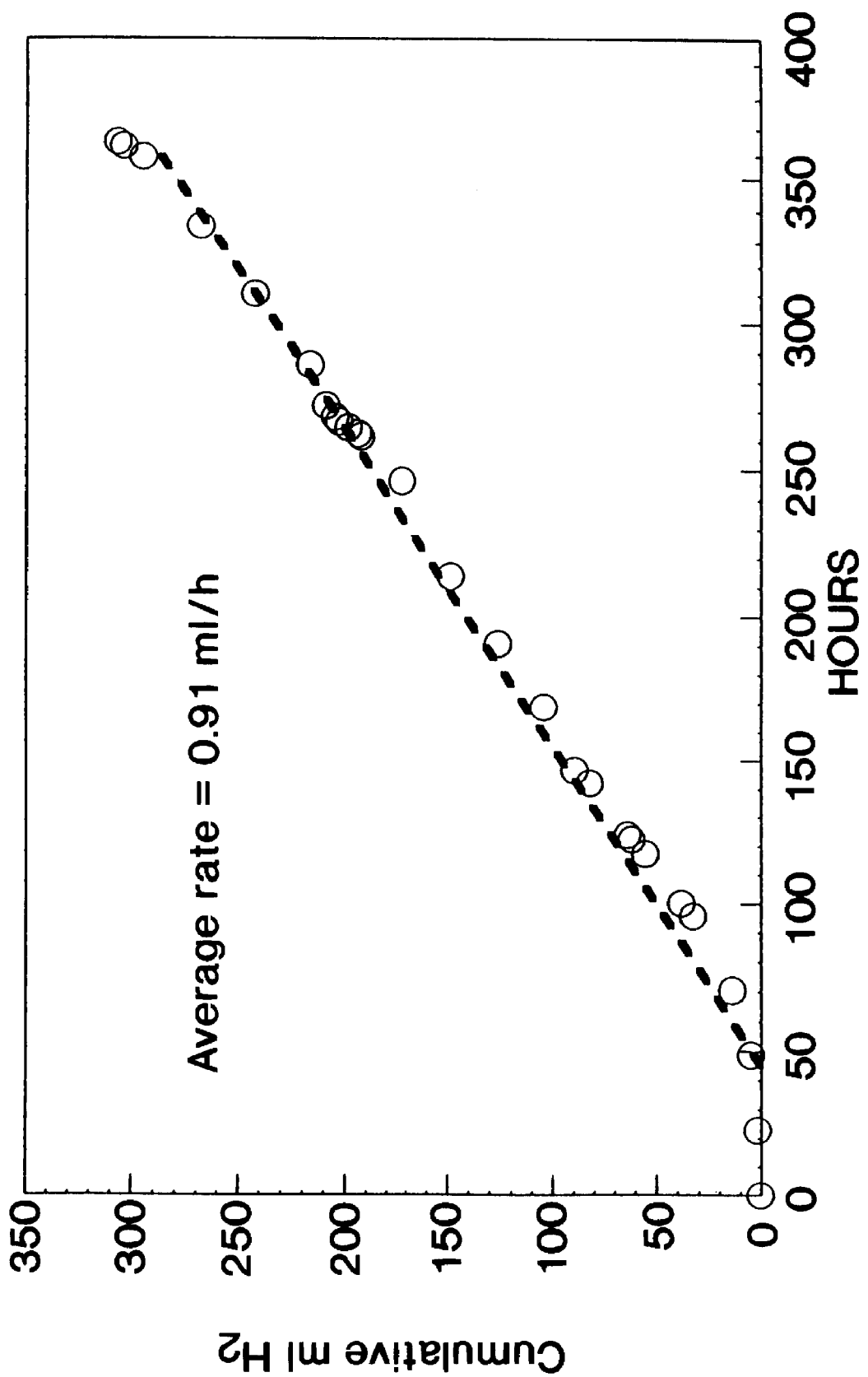
FIG. 11 is a graph showing sustained production of hydrogen by FOX1 over time at 30 mM formate.
Figure 12:
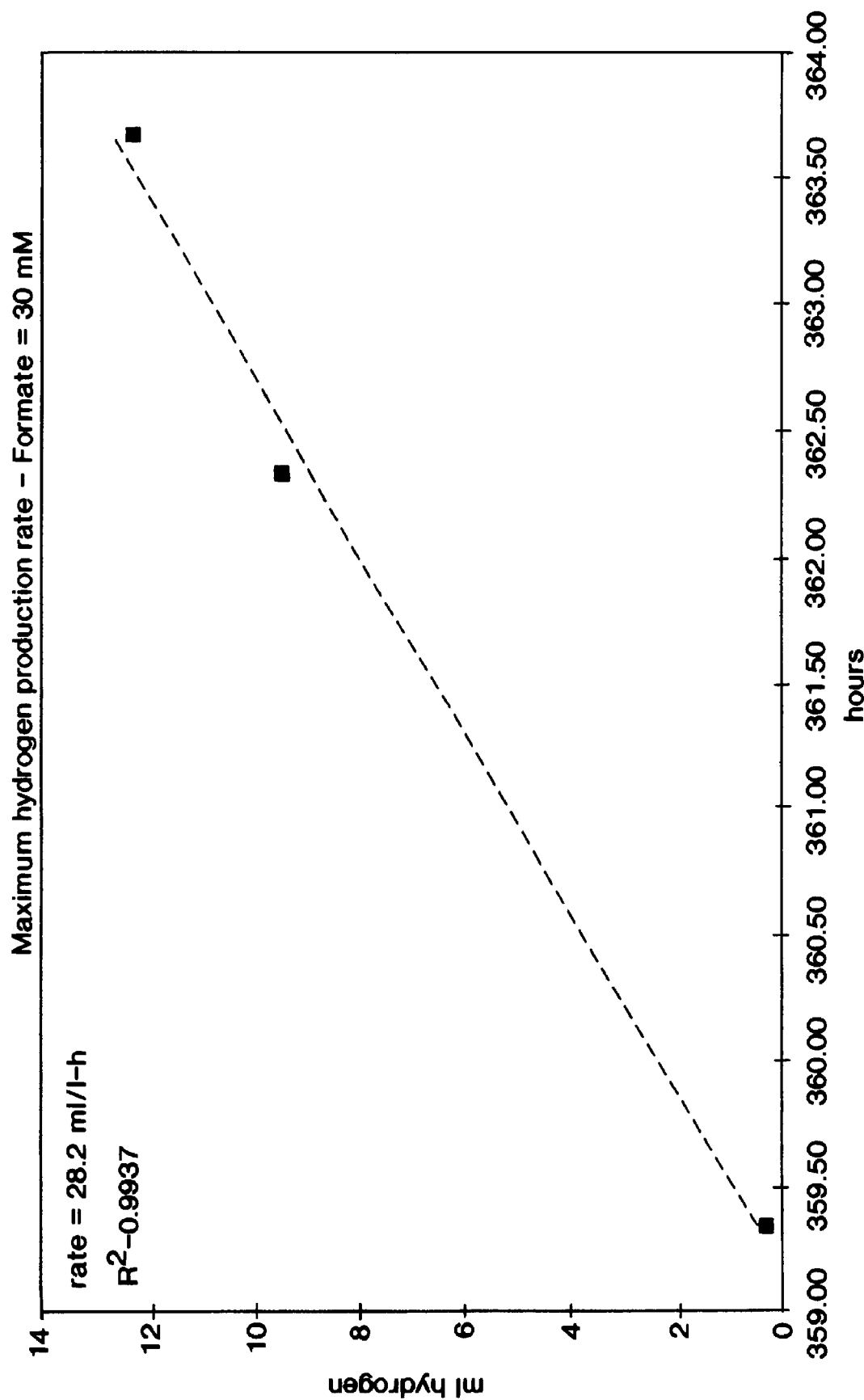
FIG. 12 is a graph showing the maximum production rate as shown in FIG. 11.
Figure 13A:
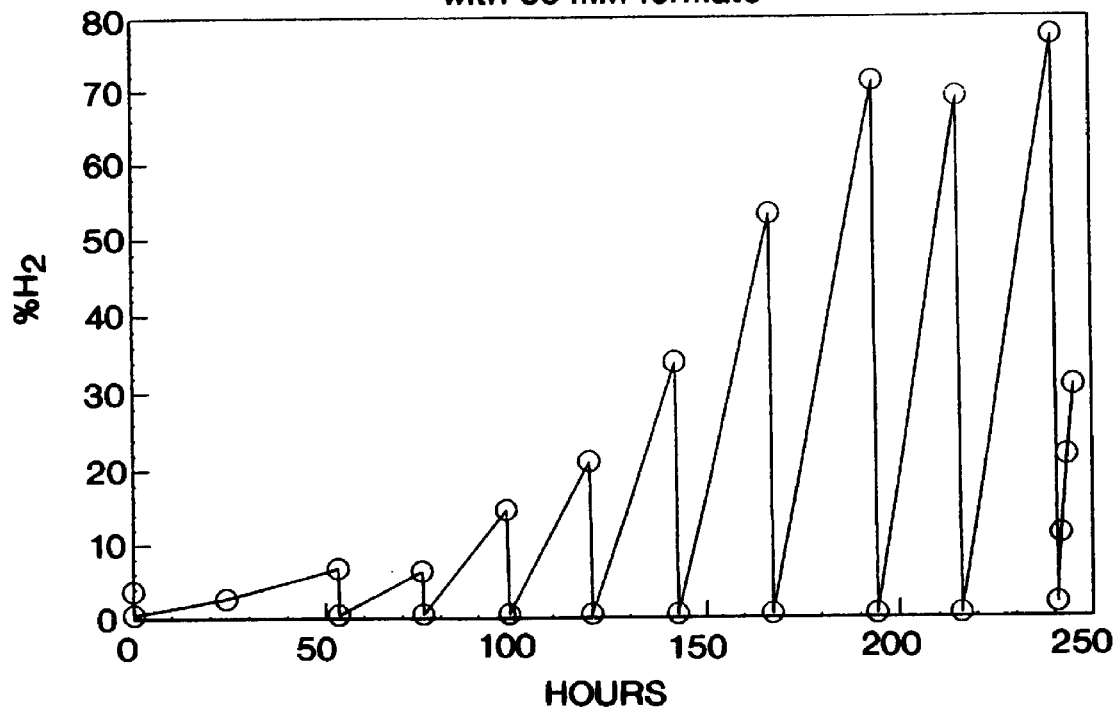
FIG. 13A is a graph showing the percent hydrogen produced at 50 mM formate with FOX1.
Figure 13B:
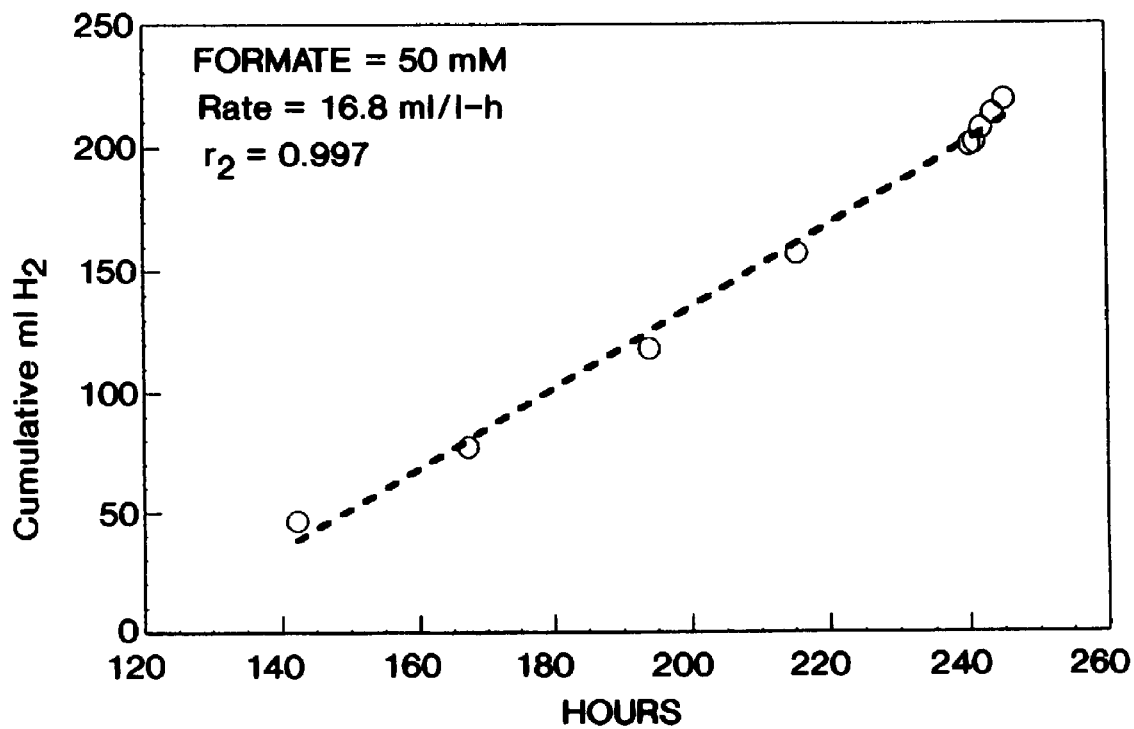
FIG. 13B is a graph showing the rate of production of hydrogen from the experiment of FIG. 13A.
Figure 14A:
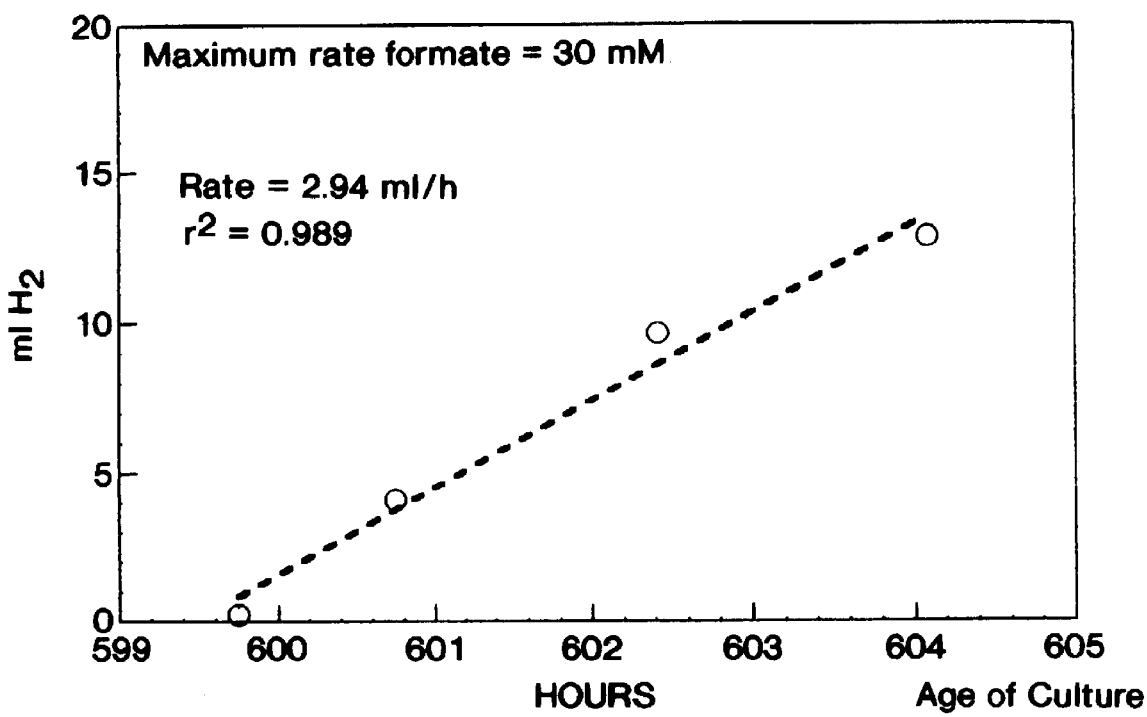
FIG. 14A is a graph showing the maximum rate of hydrogen production at 30 mM formate with FOX1.
Figure 14B:
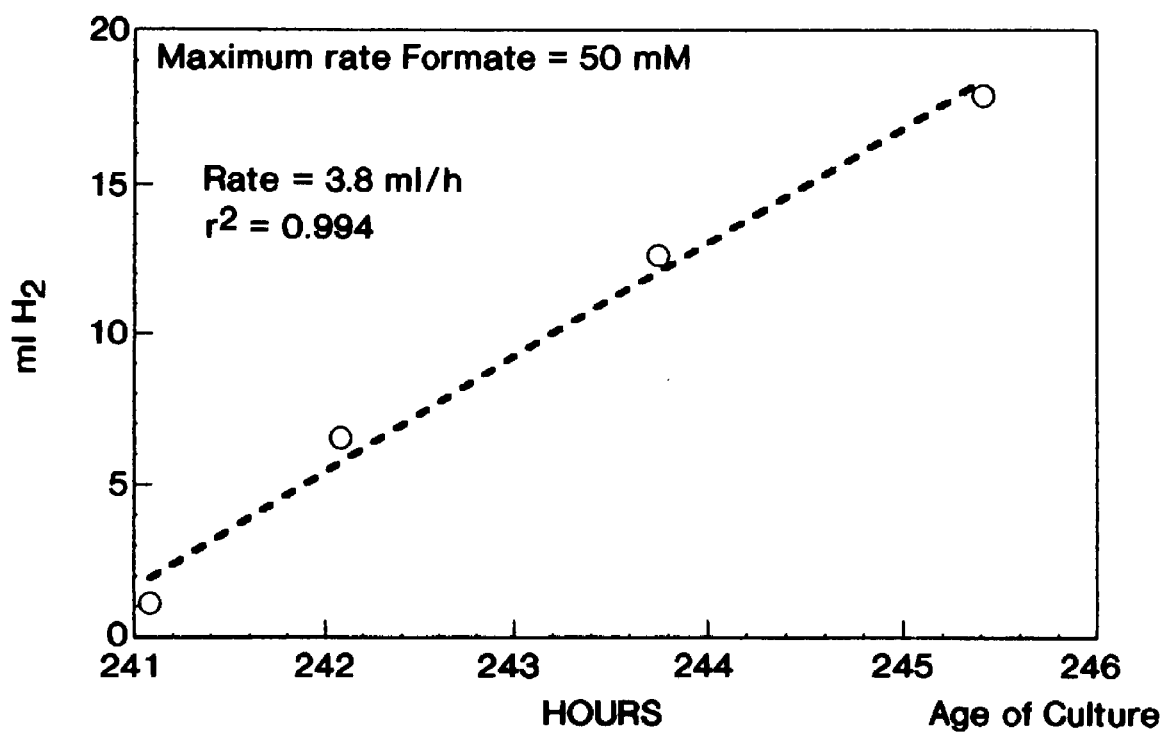
FIG. 14B is a graph showing the rate of hydrogen production at 50 mM formate under the same growth conditions as FIG. 14A.

Formate oxidation and subsequent release of $H_2$ is sustained over long periods of time with increases in rate proportional to increases in biomass (FIGS. 10A and 10B). FIG. 10B shows that cultures which are maintained at a constant formate concentration of 30 mM will continue to produce hydrogen at fairly high rates as long as the headspace is purged periodically. This corresponds to a physical manipulation of the culture that results in the lowering of the $\Delta G'$. Since this culture grows at the expense of formate oxidation to hydrogen it is likely that this activity can be maintained on a continuous basis in a bioreactor.

FIGS. 11 to 15 show various aspects of the hydrogen production under a variety of conditions as well as the change of $\Delta G$.

Based upon Example 6, the following are estimates of $H_2$ production rates:

Maximum rate (100 ml vol): (1) Growth experiment yields 7.27 μmoles/h; 0.16 ml/h (2) Fed batch experiment yields 64.7 μmoles/h; 1.45 ml/h;

(3) Number of cells in culture: Growth experiment yields $2 \times 10^6$ cells per ml;

Fed batch experiment yields approx. 10 times more.

(4) Assumed mass of cells: Growth experiment $10^{12}$ cells per gram dry weight yields 0.0002 g cells;

(5) Rate of $H_2$ production: Growth experiment yields 0.6 moles/g-min or 13.4 liters per g-min.

EXAMPLE 7

Figure 17:
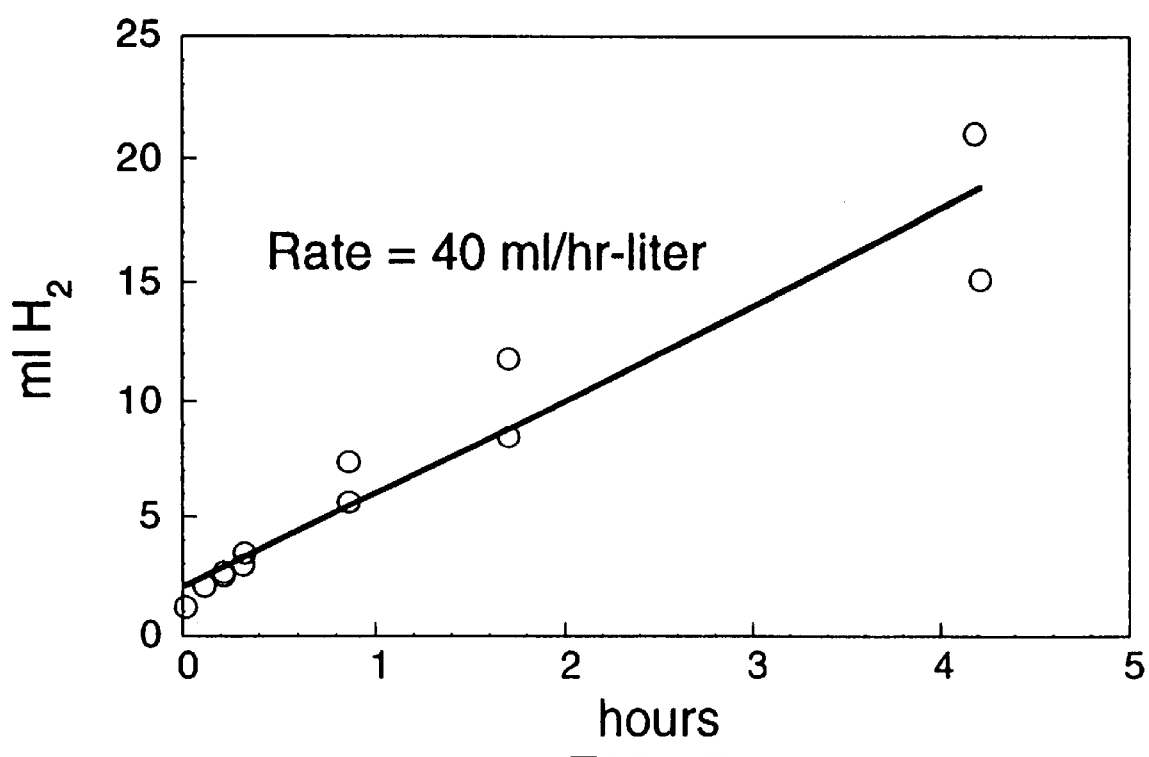
FIG. 17 is a graph showing rate of $H_2$ generation in duplicate FOX1 cultures over a four hour period after purging the headspace.

Optimal conditions for FOX1 hydrogen generation:

Maximum hydrogen generation was measured in duplicate FOX1cultures. $H_2$ was produced maximally (65 ml/hr-liter) during the first twenty minutes after the purging of the headspace with Argon and the addition of formic acid (FIG. 15). The rate of $H_2$ generation was sustained at a lower rate of 40 ml/hr-liter over a four hour period (FIG. 17). The addition of formic acid typically lowered the pH of the cultures to less than 4.8 and facilitated the removal of $CO_2$ during the argon purging of the headspace. It was important to remove $CO_2$, since formate oxidation was more favorable energetically when all products are removed. Formic acid addition also neutralizes the corresponding increase in pH due to the production of $H_2$, which removes $H^+$ from the culture.

Figure 18:
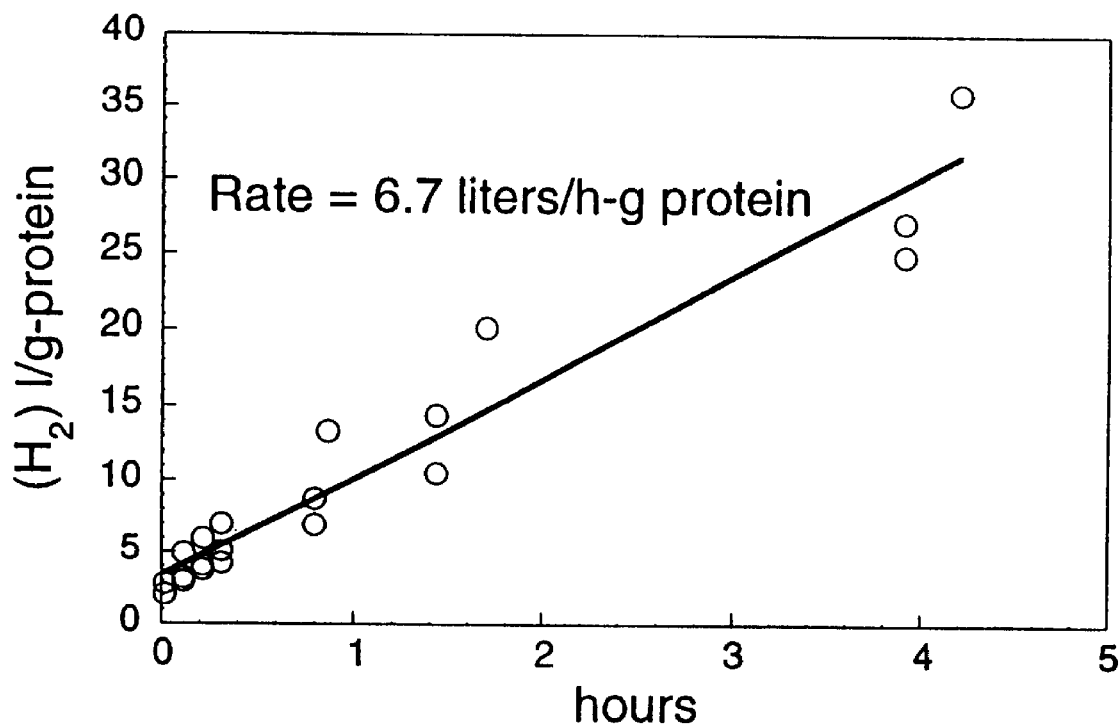
FIG. 18 is a graph showing hydrogen production by triplicate FOX1 cultures expressed as a function of biomass protein as bovine serum albumin (BSA).
Figure 19:
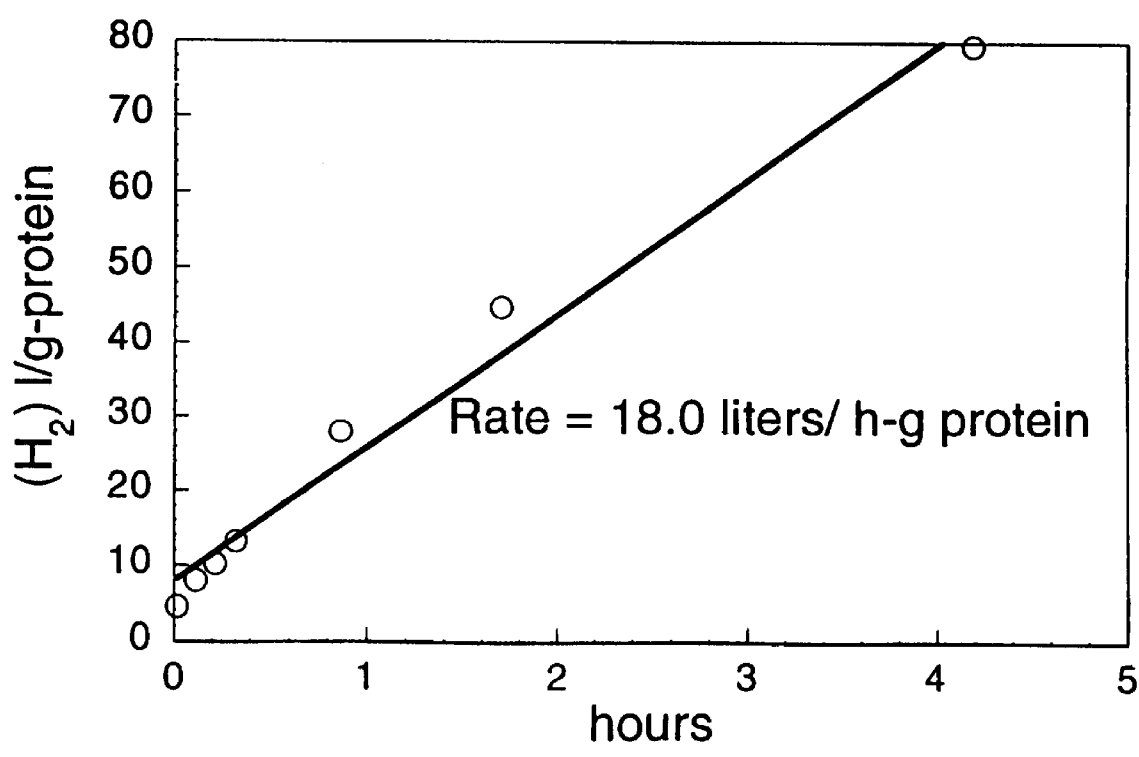
FIG. 19 is a graph showing maximum $H_2$ production observed in single FOX1 culture on a per gram biomass protein (as BSA).

The maximum $H_2$ production rate can also be expressed in terms of biomass. This is more useful when comparing to other $H_2$ production methods. FIG. 18 shows that triplicate cultures exhibited an averaged rate of $H_2$ production of 6.7 l/h-g protein (as bovine serum albumin BSA). Even higher rates were observed in a single younger culture of FOX1, which evolved $H_2$ at a rate of 18 l/h-g protein (FIG. 19). The yield of cell biomass was determined to be 20.9 mg protein as BSA per mole of formate oxidized. The measurement of increased protein production coupled to formate oxidation serves as confirmation of the uniqueness of growth exhibited by FOX1 under $H_2$ producing conditions.

COMPARATIVE EXAMPLE 8

Hydrogen generation by other δ-Proteobacteria:

Three ATCC strains of Desulfovibrio were tested for the ability to produce $H_2$ and/or grow from formate oxidation. The strains chosen, *D. gigas*, *D. desulfuricans*, and *D. africanus*, were the closest phylogenetically to FOX1. None of these strains appeared to grow using formate as the sole energy source, however pregrown cells of all three strains produced significant amounts of $H_2$ from formate. The strains tested did not catalyze formate oxidation to thermodynamic equilibrium, as occurs with FOX1. *D. desulfuricans* was able to produce the most $H_2$ reaching 0.2 atm on formate alone. There is evidence presented in the literature that *Desulfomonile tiedjei* DCB-1 does generate $H_2$ from formate and catalyzes this reaction to thermodynamic equilibrium (DeWeerd et al., Applied and Environ. Microb. 57:1929–1934 (1991)). It has not been determined whether DCB-1 is able to couple growth to this reaction. Since DCB-1 has little similarity to FOX1 phylogenetically, but both are in the δ-Proteobacteria, it is reasonable to propose that the ability to generate $H_2$ from formate may be distributed throughout this group of organisms, but only at relatively low levels.

Figure 16:
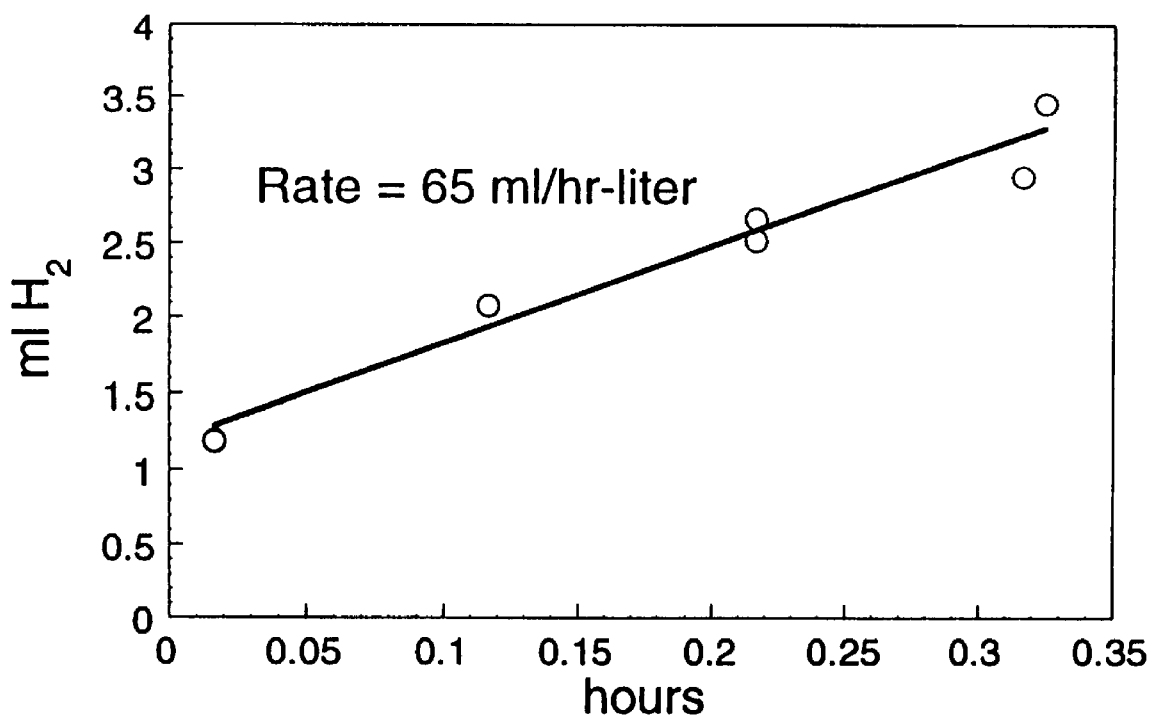
FIG. 16 is a graph showing the rate of hydrogen generation in duplicate FOX1 cultures during first 20 minutes after purging.
Figure 20:
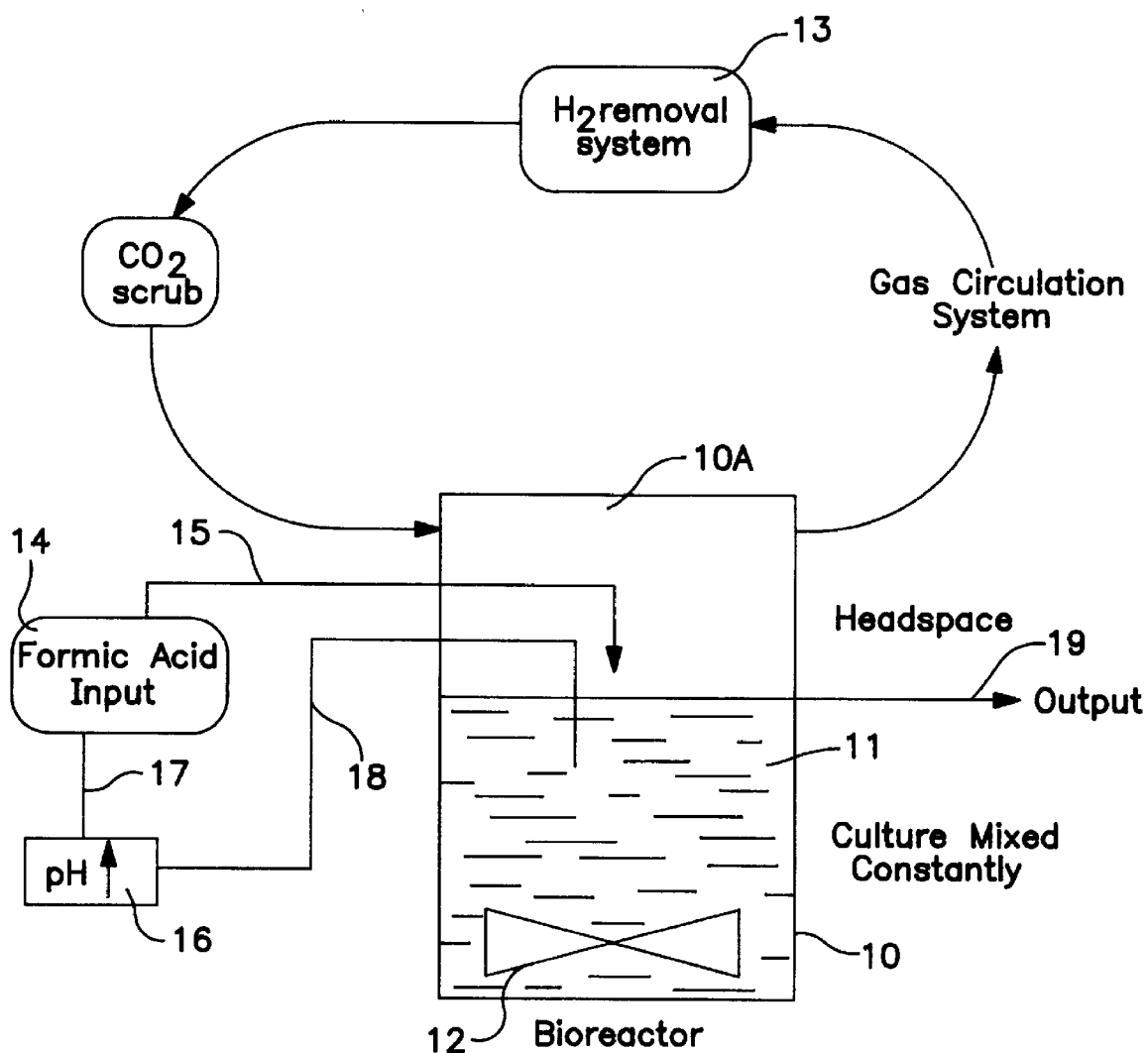
FIG. 20 is a schematic view of a system for hydrogen production by formate oxidizing culture in a bioreactor 10. Formic acid input is controlled by the increase in pH, as in a pH-auxostat. Gas in headspace 10A is either continuously scrubbed or periodically scrubbed of $H_2$ and $CO_2$ depending on optimal operating conditions.

A bioreactor 10 that facilitates the separation of hydrogen from carbon dioxide is preferred such as shown in FIG. 16. FIG. 16 shows the bioreactor 10 wherein a culture 11 which is mixed by mixer 12. A hydrogen removal system 13 is used to remove hydrogen from calcium dioxide for headspace 10A. A container 14 is used to feed formic acid or formate to the bioreactor 10 by line 15. The pH of the culture medium 11 is controlled by a chemical source 16 and lines 17 and 18. Spent culture medium 11 can be removed by line 19. This can be achieved by taking advantage of the density differences between these two gases, perhaps facilitated by cooling the headspace of the bioreactor. Another possibility is using diffusion membranes that will exclude, to a large extent, molecules the size of $CO_2$. The bioreactor can be operated as a pulse fed system with pH controlling the flow of fresh formic acid-containing media. The acid will lower the pH and increase the headspace concentration of $CO_2$, which will be subsequently flushed to remove the product gases and maintain optimal growth conditions (i.e. low $\Delta G'$) A preferred scheme is shown in FIG. 20.

The role of formate in anaerobic food webs, particularly its possible role in interspecies electron transfer, should be reevaluated. For example in a methanogenic ecosystem with a significant formate flux, the formate oxidation to methane and $CO_2$ can actually support the growth of two microbial populations: the $H_2$ producer and the methanogen (FIG. 2). The only requirement for this type of consortium to function is to not have formate in equilibrium with $H_2$ and $CO_2$. Such an environment was described by McMahon and Chapelle (Nature 349:233–235 (1991)) when they found that high concentrations of formic and acetic acid are produced in aquitard sediments and subsequently diffuse into anaerobic sulfidogenic and methanogenic aquifer material. Since $H_2$ concentrations in such anaerobic environments are kept very low by methanogenesis and sulfate reduction, the oxidation of formate to $H_2$ would be thermodynamically favorable. Therefore reasonable conditions do exist in the natural environment for the anaerobic oxidation of formate to hydrogen.

Formate can be produced biocatalytically from oxalate for use in the process of the present invention. Such processes are shown in Smith, et al. Arch. Microbiol. 141:8–13 (1985); Allison et al. Arch Microbiol. 141:1–7 (1985); and Applied and Environ. Microbiol. 58:1451–1458 (1992).

It is intended that the foregoing description be only illustrative of the present invention and that the present invention be limited only by the hereinafter appended claims.

We claim:

1. A method for remediating an environment containing a first carbon source selected from the group consisting of formic acid, formate and mixtures thereof which comprises:

introducing a delta-proteobacterium having all of the identifying characteristics of ATCC 55738 (FOX1) into the environment so that hydrogen is produced in the environment which is utilized by a second bacterium in the environment.

2. The method of claim 1 wherein a second additional carbon source is provided with the first carbon source.

3. The method of claim 1 wherein the delta-proteobacterium is deposited strain ATCC 55738.

4. The method of claim 1 wherein the formate is produced by anaerobic fermentation of oxalate by the second bacterium.

5. The method of claim 1 wherein the first carbon source is produced by an enzymatic reaction with oxalate.

6. The method of claim 1 wherein a culture medium is the environment and is shaken during the utilization.

7. The method of claim 1 wherein carbon dioxide is produced and wherein the hydrogen and the carbon dioxide are removed from the environment during the utilization.

8. The method of claim 1 wherein carbon dioxide is produced and wherein the hydrogen and the carbon dioxide are removed from the environment periodically during the growing of the bacterium.

9. The method of claim 1 wherein a culture medium is the environment and contains between about 10 and 40 mM of the first carbon source.

10. The method of claim 1 wherein the formate is present as sodium formate, wherein a culture medium as the environment contains a reductant selected from the group consisting of sodium cysteine and sodium sulfide; ammonia chloride as the nitrogen source, sodium bicarbonate as a buffer, and sodium acetate as a second carbon source and wherein the confined space is supplied with an inert gas and carbon dioxide.

11. The method of claim 1 wherein a culture medium is the environment and has a pH between about 4 and 8.

12. The method of claim 1 wherein a culture medium is the environment and has a pH between about 4 and 8.

13. The method of claim 1 wherein a culture medium is the environment and contains a reductant selected from the group consisting of sodium cysteine and sodium sulfide.

14. The method of claim 1 wherein an acetate salt as a second carbon source is provided with the first carbon source.

* * * * *